(12) United States Patent
Krainc

(10) Patent No.: US 7,045,306 B2
(45) Date of Patent: May 16, 2006

(54) METHOD FOR IDENTIFYING COMPOUNDS IN VITRO THAT MODULATE THE DYSREGULATION OF TRANSCRIPTION OF TRANSCRIPTION MEDIATED BY MUTANT HUNTINGTIN PROTEIN

(75) Inventor: Dimitri Krainc, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 42 days.

(21) Appl. No.: 10/425,175

(22) Filed: Apr. 28, 2003

(65) Prior Publication Data

US 2004/0213780 A1 Oct. 28, 2004

(51) Int. Cl.
G01N 33/567 (2006.01)
C12Q 1/68 (2006.01)
C12Q 1/00 (2006.01)
C12N 15/00 (2006.01)
C12N 15/09 (2006.01)

(52) U.S. Cl. ............................. 435/7.21; 435/6; 435/4; 435/320.1; 514/44; 424/93.1; 536/23.1; 536/23.53

(58) Field of Classification Search ................ 536/23.1, 536/23.53; 514/44; 435/320.1, 6; 424/93.1
See application file for complete search history.

(56) References Cited

U.S. PATENT DOCUMENTS

2002/0137663 A1* 9/2002 Forman et al. ................. 514/1

OTHER PUBLICATIONS

Dunah, et al. (2002) Science, 296: 2238-43.*
Freiman, et al. (2002) Science, 296: 2149-50.*
Garret, et al. (1995) Biochemistry, Published by Saunders College Publishing, pp. 970-975.*
Langer (2003) Scientific American, 288(4): pp. 50-57.*
Albright, S.R. et al., TAFs revisited: more data reveal new twists and confirm old ideas. Gene, 242:1-13, 2000.
Augood, S.J. et al., Dopamine D1 and D2 receptor gene expression in the striatum in Huntington's disease. Ann. Neurol., 42: 215-221, 1997.
Chiang, C.M. et al., Cloning of an intrinsic human TFIID subunit that interacts with multiple transcriptional activators. Science, 267: 531-536, 1995.
Cooper, J.K., et al., Truncated N-terminal fragments of huntingtin with expanded glutamine repeats form nuclear and cytoplasmic aggregates in cell culture. Hum. Mol. Genet., 7: 783-790, 1998.
Dikstein, R. et al., Human TAFII 105 is a cell type-specific TFIID subunit related to hTAFII130. Cell, 87: 137-146, 1996.
Dunah, A.W. et al., Subunit composition of N-methyl-D-aspartate receptors in the central nervous system that contain the NR2D subunit. Mol. Pharmacol., 53: 429-437, 1998.

Furukawa, T. et al., Assembly of partial TFIID complexes in mammalian cells reveals distinct activities associated with Individual TATA box-binding protein-associated factors. J. Biol. Chem., 275: 29847-29856, 2000.
Gangloff, Y.G. et al., The human TFIID components TAF(II)135 and TAF(II)20 and the yeast SAGA components ADA1 and TAF(II)68 heterodimerize to form histone-like pairs. Mol. Cell Biol., 20: 340-351, 2000.
Gutekunst, C.A., et al., Nuclear and neuropil aggregates in Huntington's disease: relationship to neuropathology. J. Neurosci., 19: 2522-2534, 1999.
Huang, C.C. et al., Amyloid formation by mutant huntingtin: threshold, progressivity and recruitment of normal polyglutamine proteins. Somatic Cell Mol. Genet., 24: 217-233, 1998.
Hughes, R.E. et al., Therapeutic opportunities in polyglutamine disease. Nature Medicine, 7: 419-423, 2001.
Kazantsev, A. et al., Insoluble detergent-resistant aggregates form between pathological and nonpathological lengths of polyglutamine in mammalian cells. Proc. Natl. Acad. Sci USA, 96: 11404-11409, 1999.
Kegel, K.B. et al., Huntingtin is present in the nucleus, interacts with the transcriptional corepressor C-terminal binding ptotein, and represses transcription. J. Biol. Chem., 277: 7466-7476, 2002.
Krainc, D. et al., Synergistic activation of the N-methyl-D-aspartate receptor subunit 1 promoter by myocyte enhancer factor 2C and Sp 1. J. Biol. Chem., 273: 26218-26224, 1998.
Lahiri, D.K. Electrophoretic mobility shift assay for the detection of specific DNA-protein complex in nuclear extracts from the cultured cells and frozen autopsy human brain tissue. Brain Res. Protoc., 5: 257-265, 2000.
Li, H. et al., Amino-terminal fragments of mutant huntingtin show selective accumulation in striatal neurons and synaptic toxicity. Nature Genet., 25: 385-389, 2000.
Li, S.H. et al., Interaction of Huntington disease protein with transcriptional activator Sp 1. Mol. Cell Biol., 22: 1277-1287, 2002.
Li, S.H. et al., Aggregation of N-terminal huntingtin is dependent on the length of its glutamine repeats. Hum. Mol. Genet., 7: 777-782, 1998.
Luthi-Carter, R. et al., Decreased expression of striatal signaling genes in a mouse model of Huntington's disease. Hum. Mol. Gen., 9: 1259-1271, 2000.

(Continued)

Primary Examiner—Dave Trong Nguyen
Assistant Examiner—Robert M. Kelly
(74) Attorney, Agent, or Firm—Wolf, Greenfield & Sacks, P.C.

(57) ABSTRACT

The invention relates to methods and products for deregulating gene transcription in neurodegenerative disease associated with an expanded polyglutamine tract in mutant proteins. The invention is useful for preventing and treating diseases associated with expanded polyglutamine tracts, including Huntington's disease. The methods and compositions of the invention are also useful for identifying additional pharmaceutical agents for preventing and treating diseases associated with expanded polyglutamine tracts.

3 Claims, 7 Drawing Sheets

OTHER PUBLICATIONS

Luthi-Carter, R. et al., Dysregulation of gene expression in the R6/2 model of polyglutamine disease: parallel changes in muscle and brain. Hum. Mol. Gen., 11:1911-1926, 2002.

Mangiarini, L. et al., Exon 1 of the HD gene with an expanded CAG repeat is sufficient to cause a progressive neurological phenotype in transgenic mice. Cell, 87: 493-506, 1996.

Martindale, D. et al., Length of huntingtin and its polyglutamine tract influences localization and frequency of intracellular aggregates. Nature Genet., 18: 150-154, 1998.

Mende-Mueller, L.M. et al., Tissue-specific proteolysis of Huntingtin (htt) in human brain: evidence of enhanced levels of N- and C-Terminal htt fragments in Huntington's disease striatum. J. Neurosci., 21: 1830-1837 2001.

Metsis, M. et al., Cell-type-specific expression of the TFIID component TAF(II)135 in the nervous system. Exp. Cell Res., 269: 214-221, 2001.

Nucifora, F.C. et al., Interference by huntingtin and atrophin-1 with cbp-mediated transcription leading to cellular toxicity. Science, 291: 2423-2428, 2001.

Paulson, H.L., Toward an understanding of polyglutamine neurodegeneration. Brain Pathology, 10: 293-299, 2000.

Saluja, D. et al., Distinct subdomains of human TAFII130 are required for interactions with glutamine-rich transcriptional activators. Mol. Cell. Biol., 18: 5734-5743, 1998.

Saudou, F. et al., Huntingtin acts in the nucleus to induce apoptosis but death does not correlate with the formation of intranuclear inclusions. Cell, 95: 55-66, 1998.

Shimohata, T. et al. Expanded polyglutamine stretches interact with TAFII130, interfering with CREB-dependent transcription. Nat. Genet., 26: 29-36, 2000.

Steffan, J.S. et al., Histone deacetylase inhibitors arrest polyglutamine-dependent neurodegeneration in Drosophila. Nature, 413: 739-743, 2001.

Steffan, J.S. et al., The Huntington's disease protein interacts with p53 and CREB-binding protein and represses transcription. Proc. Natl. Acad. Sci USA, 97: 6763-6768, 2000.

Surmeier, D.J. et al., Coordinated expression of dopamine receptors in neostriatal medium spiny neurons. J. Neurosci., 16: 6579-6591, 1996.

Vonsattel, J.P. et al., Neuropathological classification of Huntington's disease. Neuropathol. Exp. Neurol., 44: 559-577, 1985.

Weeks, R.A. et al., Striatal D1 and D2 dopamine receptor loss in asymptomatic mutation carriers of Huntington's disease. Ann. Neurol., 40: 49-54, 1996.

Yajima, S. et al., Sp family transcription factors regulate expression of rat D2 dopamine receptor gene. DNA Cell Biol., 17: 471-479, 1998.

* cited by examiner

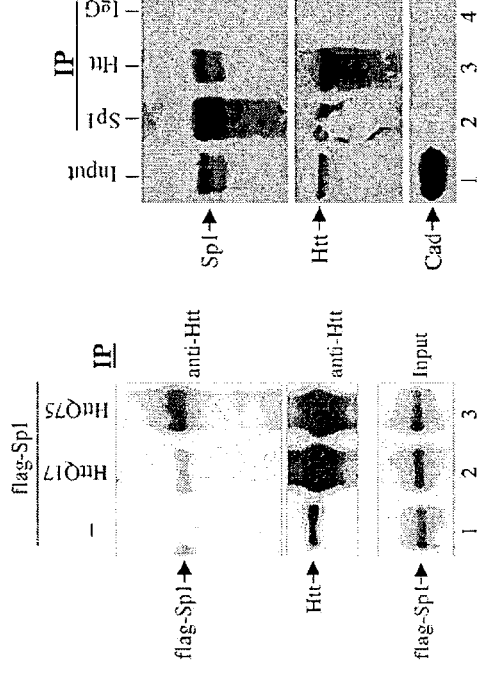
FIG. 1C
FIG. 1D
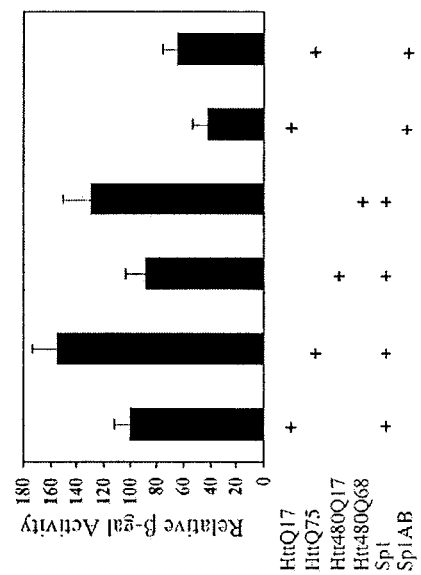
FIG. 1A
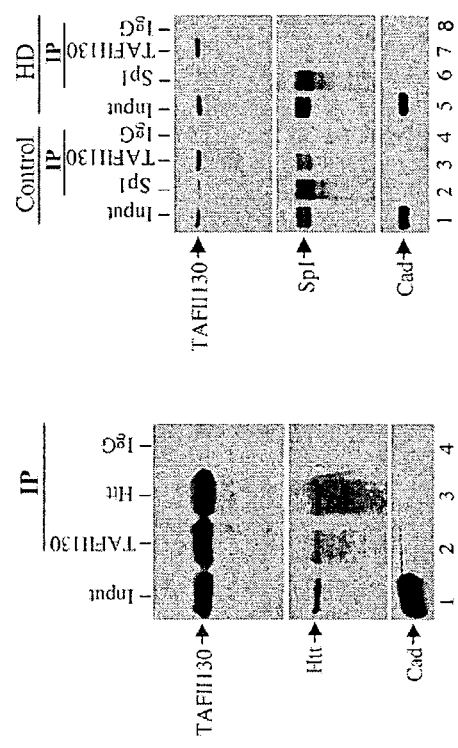
FIG. 1E
FIG. 1F
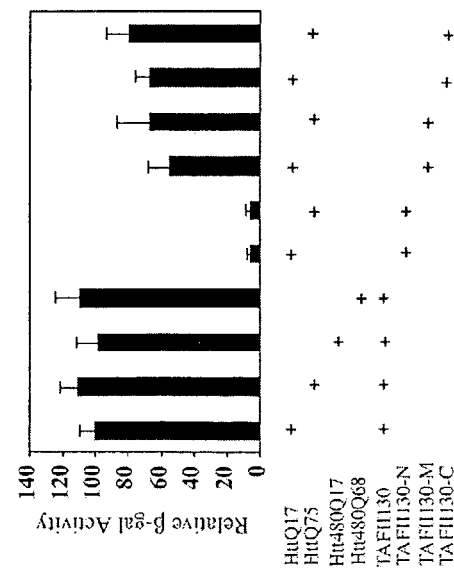
FIG. 1B

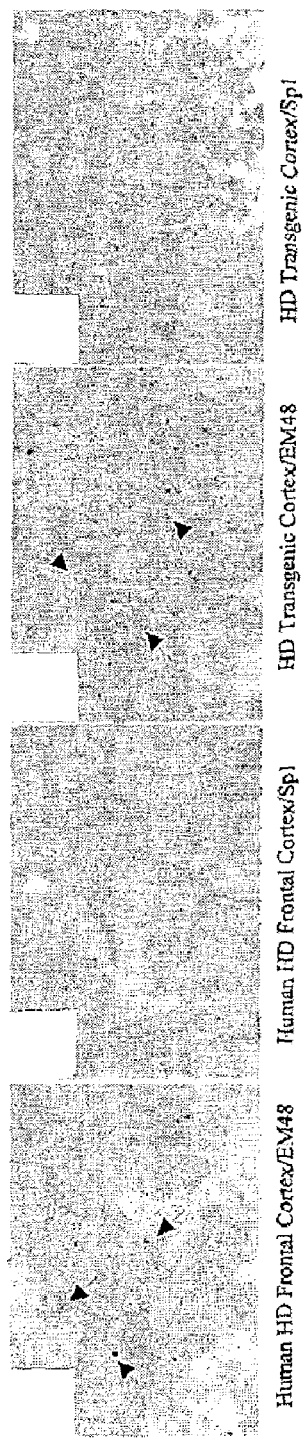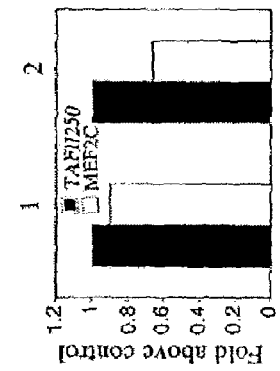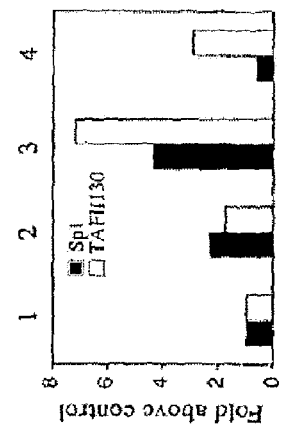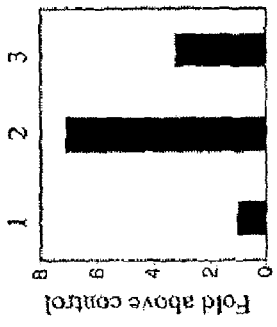
FIG. 4A  Human HD Frontal Cortex/EM48
FIG. 4B  Human HD Frontal Cortex/Sp1
FIG. 4C  HD Transgenic Cortex/EM48
FIG. 4D  HD Transgenic Cortex/Sp1
FIG. 4E
FIG. 4F
FIG. 4G

SEQUENCE LISTING

<160> NUMBER OF SEQ ID NOS: 5

<210> SEQ ID NO 1
<211> LENGTH: 24
<212> TYPE: DNA
<213> ORGANISM: Homo sapiens

<400> SEQUENCE: 1
cagggtgacc ccgcccctc ctcc                                    24

<210> SEQ ID NO 2
<211> LENGTH: 22
<212> TYPE: DNA
<213> ORGANISM: Homo sapiens

```
-continued

<400> SEQUENCE: 2
attcgatcgg ggcggggcga gc                                            22

<210> SEQ ID NO 3
<211> LENGTH: 20
<212> TYPE: DNA
<213> ORGANISM: Homo sapiens

<400> SEQUENCE: 3
gcagtcgagc tttcagagcc                                               20

<210> SEQ ID NO 4
<211> LENGTH: 21
<212> TYPE: DNA
<213> ORGANISM: Homo sapiens

<400> SEQUENCE: 4
tctgcggctc atcgtcttaa g                                             21

<210> SEQ ID NO 5
<211> LENGTH: 21
<212> TYPE: DNA
<213> ORGANISM: Homo sapiens

<400> SEQUENCE: 5
atgggctata aatagccgcc a                                             21
```

US 7,045,306 B2

METHOD FOR IDENTIFYING COMPOUNDS IN VITRO THAT MODULATE THE DYSREGULATION OF TRANSCRIPTION OF TRANSCRIPTION MEDIATED BY MUTANT HUNTINGTIN PROTEIN

GOVERNMENT SUPPORT

This invention was made in part with government support under grant number K08NS02174-03 from the National Institutes of Health (NIH). The government may have certain rights in this invention.

FIELD OF THE INVENTION

The invention relates to methods and products for modulating gene transcription in neurodegenerative disease associated with an expanded polyglutamine tract in mutant proteins. The invention is useful for preventing and treating diseases associated with expanded polyglutamine tracts, including Huntington's disease. The invention also includes methods and compounds for identifying pharmaceutical agents for preventing and treating diseases associated with expanded polyglutamine tracts, including Huntington's disease.

BACKGROUND OF THE INVENTION

A number of naturally occurring proteins have uninterrupted tracts of glutamine residues encoded by the CAG triplet repeats. It now known that the expansion of the length of these uninterrupted tracts or regions of trinucleotide repeats in proteins is associated with specific neurodegenerative diseases. The expansion of polyglutamine tracts in proteins may become pathogenic if the polyglutamine tracts expand beyond a threshold length, which for most of the polyglutamine expansion-associated disorders is a length of approximately 35–40 residues. When the threshold is reached, the presence of the abnormal protein is associated with neurodegenerative diseases such as: Huntington's disease, spinocerebellar ataxias (SCAs), spinobulbar muscular atrophy (SBMA, Kennedy disease), and dentatorubropallidoluysian atrophy (DRPLA). In each of these disorders, abnormal expanded regions of CAG repeats have been identified in the coding region of a protein.

Cellular and genetic characteristics of the polyglutamine expansion-associated disorders have begun to be elucidated. It is known that Huntington's disease is characterized by mutant huntingtin protein with abnormal expanses of polyglutamine tracts. In Spinocerebellar Ataxia Type 1 (SCA1), the ATX1 gene includes abnormal expanded CAG repeats and encodes a mutant ataxin-1 protein that contains abnormal polyglutamine stretches. A similar situation has been identified in Spinocerebellar Ataxia Type 2 (SCA2), which is characterized by abnormal expansion of CAG repeats located in the ATX2 gene. The abnormal ATX2 gene encodes mutant ataxin-2 that includes abnormal polyglutamine stretches. In spinocerebellar Ataxia Type 3 (SAC3), which is also known as Machado-Joseph disease (MJD), the mutant ATX3 gene includes abnormal numbers of CAG repeats and encodes mutant ataxin-3 protein with characteristic expanded polyglutamine stretches. Spinocerebellar Ataxia Type 7 (SCA7) is associated with an abnormal SCA7 gene that encodes mutant ataxin-7 protein with the expanded polyglutamine regions. In spinocerebellar ataxia Type 6 (SCA6) there are expanses of CAG repeats in the coding region of an isoform of the alpha-1A calcium channel subunit (CACNA1A), which are predicted to encode polyglutamine stretches in the protein. In spinobulbar muscular atrophy (SBMA), CAG repeats located in the androgen receptor gene result in abnormal polyglutamine stretches in the androgen receptor protein encoded by the gene. In DRPLA, the DRPLA gene exhibits abnormal CAG repeats and encodes mutant atropin-1 protein, which shows expanded polyglutamine stretches that are characteristic of the polyglutamine expansion-associated disorders.

Common features of polyglutamine expansion-associated diseases include the gradual loss of neurons with a concomitant loss of motor and cognitive functions, but there are clinical differences in the various diseases. For example, the onset of Huntington's disease is characterized by choreic movements that result from the selective involvement of medium spiny neurons of the striatum. In contrast, the onset of SBMA, which is an X-linked disease involving a polyglutamine tract in the androgen receptor protein (AR), is characterized by weakness and swallowing difficulties because motor neurons in the brain stem and spinal cord are selectively lost (H. L. Paulson, *Brain Pathology* 10:293–299, 2000). As each of the polyglutamine expansion-associated diseases progresses, more regions of the brain and spinal cord of the patient become involved.

The severity of the symptoms and progression of the polyglutamine expansion-associated diseases varies from patient to patient, in part due to fact that the length of the expanded polyglutamine region correlates with the severity of the symptomatic presentation. Thus, patients with longer expanded polyglutamine regions may have more severe clinical effects from the disease and may show an earlier age of onset than would patients with shorter expanded polyglutamine regions. Although there is some variation between the polyglutamine expansion-associated diseases, they all generally present symptomatically in mid to late life and all but SBMA, which is X-linked, are dominantly inherited.

The polyglutamine expansion-associated diseases are all neurodegenerative and fatal (R. E. Hughes & J. M. Olson, *Nature Medicine*, 7:419–423, 2001), and although it is possible to diagnose polyglutamine expansion-associated disorders such as Huntington's disease, there are very limited treatment options available for patients diagnosed with one of the disorders. The lack of effective treatments for polyglutamine expansion-associated disorders means that even with a definitive diagnosis, the therapeutic options are quite limited. Thus, there is a significant need for effective compounds and methods for preventing and/or treating polyglutamine expansion-associated disorders as well as a need for methods to identify candidate pharmaceutical agents useful to treat these devastating diseases.

SUMMARY OF THE INVENTION

We have determined that mutant proteins with abnormal polyglutamine expanses modulate gene transcription. For example, we have identified that in Huntington's disease mutant huntingtin with expanded polyglutamine tracts dysregulates gene transcription by disrupting coupling of transcriptional activator Sp1 with its cognate coactivator TAFII130. Such disruption of the Sp1/TAFII130 complex results in dysregulation of many genes involved in pathogenesis of Huntington's disease. Our findings show that expanded polyglutamines interfere with general transcriptional machinery that leads to dysregulation of genes in patients with polyglutamine expansion-associated disorders.

We have identified an unexpected interaction of mutant huntingtin protein with the transcriptional activator Sp1 and the coactivator TAFII130, and have determined that coexpression of Sp1 and TAFII130 reverses the transcriptional dysregulation caused by mutant huntingtin. Surprisingly, we have discovered that the co-expression of Sp1 and TAFII130 also protects neurons from huntingtin-induced cellular toxicity. Accordingly, the invention provides in certain aspects novel methods of treating HD and/or other polyglutamine expansion-associated disorders by blocking or overcoming the inhibition of transcription by Sp1 and TAFII130 that is dysregulated by mutant huntingtin protein. In addition, our data indicate that the dysregulation of gene transcription may occur prior to the onset of symptoms of the polyglutamine expansion-associated disorder. For example, the activity of transcription factors is altered in the Huntington's disease brain before patients develop clinical symptoms.

The invention also provides methods for screening potential pharmaceutical agents for activity against polyglutamine expansion-associated disease mutant proteins that dysregulate gene transcription. For example, the methods of the invention can be used to test potential pharmaceutical agents for activity against huntingtin-mediated transcriptional dysregulation, thus the invention includes methods to identify compounds that modulate transcriptional dysregulation caused by mutant huntingtin.

According to one aspect of the invention methods for treating Huntington's disease are provided. The methods include administering to a subject in need of such treatment an effective amount of a compound that reduces the inhibition of transcription by Sp1 and/or TAFII130 dysregulated by a mutant huntingtin protein.

According to another aspect of the invention, methods for treating Huntington's disease are provided. The methods include administrating to a subject in need of such treatment an effective amount of a compound that increases transcription by Sp1 and/or TAFII130. In some embodiments, the Sp1 and/or TAFII130 is part of a complex.

In some embodiments of the foregoing aspects of the invention, the subject is a human. In some embodiments of the foregoing aspects of the invention, the subject has been diagnosed with Huntington's disease or is at risk of developing Huntington's disease. In certain embodiments of the foregoing aspects of the invention, the compound is linked to a targeting molecule. In some embodiments of the foregoing aspects of the invention, the targeting molecule's target is a neuronal cell. In some embodiments of the foregoing aspects of the invention, the compound is selected from the group consisting of small molecules, polypeptides, and nucleic acids. In some embodiments of the foregoing aspects of the invention, the polypeptide is an antibody or antigen-binding fragment thereof. In some embodiments of the foregoing aspects of the invention, the nucleic acid molecule encodes a polypeptide selected from the group consisting of: Sp1 and TAFII130. In some embodiments of the foregoing aspects of the invention, the mode of administration is selected from the group consisting of: implantation, mucosal administration, injection, inhalation, and oral administration. In certain embodiments of the foregoing aspects of the invention, the compound is administered in combination with an additional drug or therapy for treating Huntington's disease.

According to another aspect of the invention, methods for identifying compounds that modulate dysregulation of transcription by Sp1 and/or TAFII130 dysregulated by mutant huntingtin protein are provided. The methods include providing an assay system comprising Sp1, TAFII130, mutant huntingtin protein and a nucleic acid comprising a Sp1 promoter operably linked to a detectable sequence, contacting the assay system with a candidate pharmacological agent, measuring the detectable sequence, wherein an change in the detectable sequence is indicative of the modulation by the candidate pharmaceutical agent of the inhibition of Sp1 and TAFII130 transcription by mutant huntingtin. In some embodiments, the assay system is in a cell. In some embodiments, the assay system is in a vessel. In certain embodiments, an increase in the detectable sequence is indicative of the inhibition by the candidate pharmaceutical agent of the inhibition of Sp1 and/or TAFII130 transcription by mutant huntingtin. In some embodiments, a decrease in the detectable sequence is indicative of the enhancement by the candidate pharmaceutical agent of the inhibition of Sp1 and/or TAFII130 transcription by mutant huntingtin. In some embodiments, the cells are neuronal cells.

According to yet another aspect of the invention, methods for treating a polyglutamine expansion-associated disease are provided. The methods include administering to a subject in need of such treatment an effective amount of a compound that inhibits dysregulation of transcription of a gene whose transcription is dysregulated by a mutant polyglutamine protein. In some embodiments, the subject is a human. In certain embodiments, the polyglutamine expansion-associated disease is selected from the group consisting of: Huntington's disease, spinocerebellar ataxias (SCA1, SCA2, SCA3/MJD, SCA6, SCA7, SCA8, SCA9, SCA10, SCA11, SCA12, SCA13, SCA14, SCA15, SCA16, SCA17, SCA18, SCA19, SCA20, SCA21, SCA22), spinobulbar muscular atrophy (SBMA, Kennedy disease), and dentatorubropallidoluysian atrophy (DRPLA). In some embodiments, the subject has been diagnosed with Huntington's disease or is at risk of developing Huntington's disease and the compound increases the level and/or activity of Sp1 and/or TAFII130 protein. In some embodiments, the subject has been diagnosed with dentatorubropallidoluysian atrophy (DRPLA) disease or is at risk of developing DRPLA and the compound increases the level and/or activity of TAFII130 protein. In some embodiments, the compound is linked to a targeting molecule. In some embodiments, the targeting molecule's target is a neuronal cell. In some embodiments, the compound is selected from the group consisting of small molecules, polypeptides, and nucleic acids. In some embodiments, the polypeptide is an antibody or antigen-binding fragment thereof. In some embodiments, the nucleic acid molecule encodes a polypeptide selected from the group consisting of: Sp1 and TAFII130. In some embodiments, the mode of administration is selected from the group consisting of: implantation, mucosal administration, injection, inhalation, and oral administration. In some embodiments, the compound is administered in combination with an additional drug or therapy for treating the polyglutamine expansion-associated disease.

BRIEF DESCRIPTION OF THE DRAWINGS

FIG. 1 provides graphs and digitized images of blots that demonstrate that Huntingtin interacts with Sp1 and TAFII130 in vitro and in human HD brain tissue. FIG. 1A is a graph of results of yeast two-hybrid experiments performed with full-length (HttQ17 and HttQ75) or truncated huntingtin constructs (Htt480Q17 and Htt480Q68) as prey against bait plasmids containing full-length Sp1 or Sp1 lacking the DNA binding domain (Sp1AB, amino acids 83 through 621). The β-galactosidase (β-gal) activity is displayed for each interaction as a percentage of the interaction between normal huntingtin and full-length Sp1 (set to 100%). Values are expressed as means±SEM. FIG. 1B is a graph of results of yeast two-hybrid experiments performed and analyzed as in FIG. 1A. TAFII130 and its derivatives containing the $NH_2$-terminal domain (TAFII130-N, amino acids 1 through 297), the glutamine-rich domain (TAFII130-M, amino acids 270 through 700), or the COOH-terminal domain (TAFII130-C, amino acids 646 through 947) were used as baits. FIG. 1C is a digitized image of a blot that demonstrations the interaction between huntingtin and Sp1 in HEK 293T cells. Wild-type huntingtin (HttQ17), mutant huntingtin (HttQ75), and FLAG-tagged Sp1 were transfected, immunoprecipitated (IP) with anti-Htt, and blotted with anti-FLAG or anti-Htt. Sp1 expression is shown on a sample of lysate (10%) used for immunoprecipitation (Input). Expressed FLAG-Sp1 and huntingtin are indicated by arrows on the left. FIG. 1D is a digitized image of a blot that shows that Huntingtin and Sp1 interact in human HD brain tissue. Total homogenate was prepared from the caudate of grade 1 human HD brain tissue and immunoprecipitated with anti-Sp1 (lane 2), anti-Htt (lane 3), or nonimmune rabbit immunoglobulins (IgG, lane 4). Lane 1 shows 10% of the input. Antibody to cadherin (Cad) was used as a control for nonspecific interaction. FIG. 1E is a digitized image of a blot that shows Huntingtin and TAFII130 interact in human HD brain tissue. Immunoprecipitations were performed as in FIG. 1D, except that anti-TAFII130 was used (lane 2). FIG. 1F is a digitized image of a blot that shows reduced Sp1-TAFII130 interaction detected in human HD brain tissue. Immunoprecipitations were performed as in FIG. 1D, except that anti-Sp1 (lanes 2 and 6) and anti-TAFII130 (lanes 3 and 7) were used for immunoprecipitations. A decrease in coprecipitated TAFII130 (upper panel, compare lanes 2 and 6) and Sp1 (middle panel, compare lanes 3 and 7) is seen in HD brain as compared with control brain tissue.

FIG. 2 provides bar graphs that demonstrate that mutant huntingtin inhibits the binding of Sp1 to DNA in vitro and in vivo.

FIG. 3 provides digitized images and graphs that illustrate that mutant huntingtin-mediated repression of the D2 receptor promoter and cell death are prevented by overexpression of Sp1 and TAFII130 in striatal cultures.

FIG. 4 provides digitized photomicrographic images of tissue sections and graphs, that illustrate the presence of increased levels of Sp1 and TAFII130 in the caudate of the human HD brain. FIGS. 4A–D are digitized photomicrographs of brain sections that show that Sp1 is not present in huntingtin-positive nuclear or cytoplasmic inclusions in human or transgenic HD brains. Immunohistochemistry using EM48, an antibody specific for huntingtin aggregates, shows labeling of inclusions (arrows) in postmortem grade 1 human HD brain tissue (frontal cortex, FIG. 4A) and transgenic mouse HD brain tissue (pyriform cortex, FIG. 4C) (K. B. Kegel, et al., *J Biol. Chem.* 277:7466, 2002).

Adjacent sections (FIGS. 4B and 4D, respectively) show diffuse nuclear and cytoplasmic localization of Sp1 but no evident localization of Sp1 in huntingtin aggregates. FIG. 4E is a graph showing that levels of Sp1 protein are increased in the caudate nucleus of grade 1 and grade 4 HD brains. Soluble protein fractions were collected from the caudate nucleus of a human control brain (lane 1), from a grade 1 HD brain (lane 2), and from a grade 4 HD brain (lane 3), and Western blot analysis was performed. Densitometric analysis shows that in grade 1 HD brain tissue as compared to control brain tissue, Sp1 levels are increased by 6.1 fold (compare lanes 1 and 2) and in grade 4 HD brain tissue by 2.8 fold (compare lanes 1 and 3). The brain samples used in each group were derived from postmortem tissue described in FIG. 2C. Densitometric analysis was corrected for differences in the expression of tubulin. Values are shown as fold above control. FIG. 4F is a graph that shows expression levels of Sp1 and TAFII130 in different regions of an HD brain. Postmortem brain tissues were processed and analyzed as in FIG. 4E. As compared with the control brain (caudate) (lane 1), the HD brain has increased Sp1 protein in the caudate nucleus (lane 3) and cerebral cortex (lane 2) but decreased Sp1 protein in the hippocampus (lane 4). TAFII130 expression follows a similar pattern as Sp1, except that only the caudate nucleus shows a marked increase in TAFII130 expression levels (compare lanes 1 and 3). FIG. 4G is a graph that shows expression of MEF2C and TAFII250 in human HD brain tissue. Tissues were processed and analyzed as in FIG. 4E. Expression of TAFII250 was not different in control (lane 1) and HD brains (lane 2), whereas MEF2C levels showed about a 30% decrease in HD brain tissue.

DETAILED DESCRIPTION OF THE INVENTION

Figure 2D:
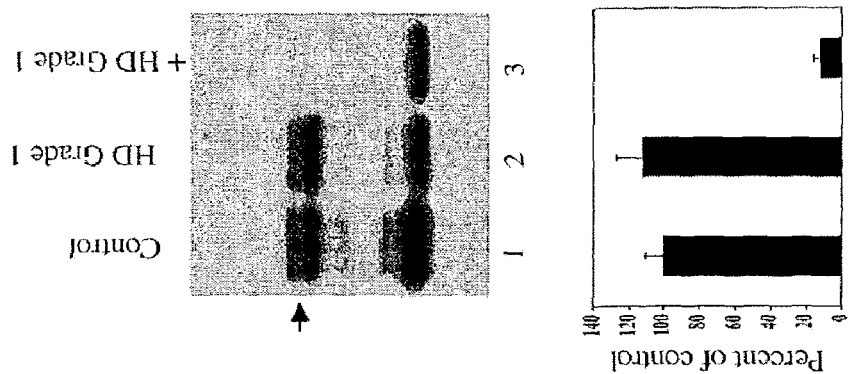
FIG. 2D is a bar graph indicating that binding of Sp1 to the D2 promoter fragment in the hippocampus of HD brain (lane 2) was not significantly altered as compared to control (lane 1). EMSA was performed as in FIG. 2C. Competition with unlabeled probe is shown in lane 3. Densitometry was used to quantify the band intensities for the graphs. Values are expressed as percent of Sp1 binding shown in lane 1 and represent means±SEM of three independent experiments, *P<0.001 for comparison with lane 1 in (A), *P<0.01 in FIGS. 2B and C.

The physiological processes associated with polyglutamine expansion-associated diseases include the dysregulation (e.g., repression) of transcription by mutant proteins that contain expanded polyglutamine regions. An example of transcription dysregulation is seen in Huntington's disease in which mutant huntingtin protein inhibits transcription of proteins. It has now been discovered that polyglutamine tract-containing proteins interact with transcriptional activators and co-activators, thereby modulating transcription. In particular, it has been discovered that mutant huntingtin interacts with Sp1 and TAFII130 and inhibits protein transcription. The mutant huntingtin-induced inhibition can be reversed by increasing the level and/or activity of the transcriptional activator Sp1 and the coactivator TAFII130. For example, the increased expression of Sp1 and TAFII130 can reverse the transcriptional inhibition caused by mutant huntingtin protein, and can also protect cells (e.g. neurons) from huntingtin-induced cellular toxicity.

As used herein, the term "polyglutamine expansion-associated disease" includes Huntington's disease, spinocerebellar ataxias (e.g. SCA1, SCA2, SCA3/MJD, SCA6, SCA7, SCA8, SCA9, SCA10, SCA11, SCA12, SCA13, SCA14, SCA15, SCA16, SCA17, SCA18, SCA19, SCA20, SCA21, SCA22), spinobulbar muscular atrophy (SBMA, Kennedy disease), dentatorubropallidoluysian atrophy (DRPLA), and other diseases associated with proteins with expanded polyglutamine regions. As used herein, the term "polyglutamine protein" means a mutant protein that contains one or more expanded polyglutamine regions. For example, in Huntington' disease, SCA1, SCA2, SCA3/MJD, SCA6, SCA7, SCA17, SBMA, and DRPLA, the polyglutamine proteins are mutant huntingtin, mutant ataxin-1, mutant ataxin-2, mutant ataxin-3, mutant alpha-1A calcium channel subunit (CACNA1A), mutant ataxin-7, mutant TATA-binding protein (TPB), mutant androgen receptor, and mutant atropin-1, respectively, each of which has an expansion of a polyglutamine sequence. As used herein, the term "non-mutant polyglutamine protein" means the normal, control, wild-type form of a polyglutamine protein, i.e., one that does not contain an expanded polyglutamine region that contributes to a polyglutamine expansion-associated disorder.

It will be understood that the number of glutamine repeats present in a polyglutamine protein can vary from subject to subject but the polyglutamine protein will still be considered to be mutant polyglutamine protein because it has an expanded polyglutamine region as compared to a normal, non-mutant polyglutamine protein. For example, non-mutant huntingtin protein encoded by DNA with from about 10 to about 35 copies of CAG will have a polyglutamine stretch, but a huntingtin protein encoded by DNA with more than about 35 copies of CAG will have an expanded polyglutamine stretch and is a mutant huntingtin protein. One of ordinary skill will be able to determine whether the number of polyglutamines in a protein is a number that indicates the protein is a mutant or non-mutant polyglutamine protein. A mutant polyglutamine protein has abnormal function and/or activity or an additional activity or function as compared to the non-mutant polyglutamine protein, (e.g., interaction with Sp1 and /or TAFII130).

The methods and compositions of the invention involve compounds that modulate the gene transcription dysregulation that is mediated (caused) by a mutant polyglutamine protein. In some diseases the dysregulation results in a reduction in transcription of one or more genes. For example, in Huntington's disease, dysregulation by mutant huntingtin protein results in a reduction in gene transcription, e.g. transcriptional repression. In other diseases dysregulation results in an increase in transcription of one or more genes. In each case, the mutant polyglutamine protein mediates the dysregulation of the transcription of the gene.

As used herein, the term "dysregulation" means the alteration of normal regulation of transcription. In some embodiments, the dysregulation of transcription is the repression of transcription and in other embodiments, the dysregulation of transcription is the enhancement of transcription. The repression of transcription results in a decrease in the level of transcription of a gene versus a control level of transcription of the gene in a cell, tissue, or subject. The enhancement of transcription results in an increase in the level of transcription of a gene versus a control level of transcription of the gene in a cell, tissue, or subject.

As used herein, the term "subject" means any mammal that may be in need of treatment with the dysregulation-modulating compounds of the invention. Subjects include but are not limited to: humans, non-human primates, cats, dogs, sheep, pigs, horses, cows, rodents such as mice, hamsters, and rats.

As used herein, the term "dysregulation-modulating compound" means a compound that modulates the transcription of a gene in a subject. In some embodiments of the invention, a dysregulation-modulating compound is a compound that increases transcription of one or more genes, and in other embodiments of the invention, a dysregulation-modulating compound is a compound that decreases transcription of one or more genes. It will be understood that the modulation of dysregulation by the compound can either be done through direct interaction with the gene or may be done indirectly through the modulation of a level and/or activity of a transcription-associated molecule (e.g. protein, nucleic acid, etc.) in a cell, tissue, or subject. For example, in Huntington's disease, a dysregulation-modulating compound may be used to indirectly reduce the inhibition of transcription caused by mutant huntingtin protein by modulating the level of Sp1 and/or TAFII130 proteins, or the activity of Sp1 and/or TAFII130 proteins or a complex of proteins including Sp1 and/or TAFII130. As used herein, the term "transcription-associated" means "involved with transcription". Thus, for example a transcription-associated protein, is a protein that is involved with transcription.

The methods of the invention involve the administration of compounds that modulate either directly or indirectly the dysregulation of transcription in cells and/or tissues, and therefore are useful to reduce or prevent the effects of a polyglutamine expansion-associated disease, for example, Huntington's disease. Examples of some genes that may be dysregulated in polyglutamine expansion-associated diseases are provided in Luthi-Carter, R. et al., *Hum Mol. Gen.* 11:1911–1926 (2002), which is hereby incorporated herein in its entirety.

In some embodiments of the invention, modulating dysregulation of transcription may be modulating the level, stability, and/or activity of a protein associated with transcription of a gene whose transcription is dysregulated by a mutant polyglutamine protein. In these embodiments, the level of expression, functional activity, and/or stability of one or more proteins that are associated with transcription of a gene whose transcription is dysregulated by a mutant polyglutamine protein may be modulated using methods such as administration of nucleic acids that encode the molecules and/or the use of binding agents, e.g. antibodies, to stabilize the proteins or complexes of one or more of the proteins.

The invention also involves a variety of assays based upon detecting the level of transcription of a gene whose transcription is dysregulated (inhibited or enhanced) by a mutant polyglutamine protein in a cell, tissue, or subject. The assays can include (1) characterizing the level of transcription of a gene whose transcription is dysregulated by a mutant polyglutamine protein in a cell and/or subject; (2) evaluating a treatment for regulating levels of transcription of a gene whose transcription is dysregulated by a mutant polyglutamine in a cell and/or subject; and/or (3) selecting a treatment for regulating the level of transcription of a gene whose transcription dysregulated by a mutant polyglutamine in a cell and/or subject. For example, an assay system that is useful in Huntington's disease may include (1) characterizing the level of gene transcription by Sp1 and/or TAFII130, or complexes that include Sp1 and/or TAFII130; (2) evaluating a treatment for regulating (e.g. increasing) levels and/or activity of gene transcription by Sp1 and/or TAFII130 or complexes that include Sp1 and/or TAFII130; and/or (3) selecting a treatment for regulating (e.g. increasing) levels and/or activity of gene transcription by Sp1 and/or TAFII130 or complexes that include Sp1 and/or TAFII130. As used herein, the term "complexes that include Sp1 and/or TAFII130" means a complex of molecules (polypeptides) that includes Sp1 and/or TAFII130.

Thus, a subject's disease can be diagnosed and/or characterized, treatment regimens can be selected and monitored, and diseases can be better understood using the assays of the present invention. For example, the invention provides in one aspect a method for measuring the level of gene transcription dysregulated by mutant polyglutamine protein in a cell and/or subject. As provided by the invention, the level of gene transcription dysregulated by mutant polyglutamine protein correlates with the existence of a polyglutamine expansion-associated disorder, e.g., Huntington's disease. For example, a level of transcription and/or activity of Sp1 and/or TAFII130, or a complex that includes Sp1 and/or TAFII130, that is significantly lower in a subject than a control level may indicate a subject has Huntington's disease, whereas a relatively normal level or transcription and/or activity of Sp1 and/or TAFII130 or a complex that includes Sp1 and or TAFII130 indicates that the subject does not have Huntington's disease.

The assays described herein are carried out on samples obtained from subjects. The samples used herein are any cell, body tissue, or body fluid sample obtained from a subject. In some embodiments, the cell or tissue sample includes neuronal cells and/or is a neuronal cell or tissue sample.

The biological sample can be located in vivo or in vitro. For example, the biological sample can be a tissue in vivo and an agent that specifically binds to a protein associated with a polyglutamine expansion-associated disorder can be used to detect the presence of such molecules in the tissue (e.g., for imaging portions of the tissue that include a mutant polyglutamine protein). Alternatively, the biological sample can be located in vitro (e.g., a biopsy such as a tissue biopsy or tissue extract). In a particularly preferred embodiment, the biological sample can be a cell-containing sample. Samples of tissue and/or cells for use in the various methods described herein can be obtained through standard methods. Samples can be surgical samples of any type of tissue or body fluid. Samples can be used directly or processed to facilitate analysis (e.g., paraffin embedding). Exemplary samples include a cell, a cell scraping, a cell extract, a blood sample, a cerebrospinal fluid sample, a tissue biopsy, including punch biopsy, a tumor biopsy, a bodily fluid, a tissue, or a tissue extract or other methods. Samples also can be cultured cells, tissues, or organs.

Particular subjects to which the present invention can be applied are subjects at risk for or known to have a glutamine expansion-associated disorder. Such disorders may include, but are not limited to: Huntington's disease, spinocerebellar ataxias (e.g., SCA1, SCA2, SCA3, SCA6, SCA7, SCA8, SCA9, SCA10, SCA11, SCA12, SCA13, SCA14, SCA15, SCA16, SCA17, SCA18, SCA19, SCA20, SCA21, SCA22), spinobulbar muscular atrophy (SBMA, Kennedy disease), dentatorubropallidoluysian atrophy (DRPLA), and any other diseases associated with polyglutamine expansion regions. The diagnostic methods of the invention are useful in advance of as well as after the onset of any clinical and/or physiological manifestation of a polyglutamine expansion-associated disease and the compounds identified using the methods of the invention can be used as therapeutics in advance of as well as after the onset of symptoms of a polyglutamine expansion-associated disorder.

The assays described herein (see Examples section) include measuring levels and/or activity of gene transcription dysregulated by mutant polyglutamine protein in a cell and/or subject. For example, the assays described herein can be used to measure the level of transcription by Sp1 and/or TAFII130 or a complex that includes Sp1 and/or TAFII130 in a Huntington's disease cell, tissue, or subject. Levels of gene transcription dysregulated by mutant polyglutamine proteins can be measured in a number of ways when carrying out the various methods of the invention. In one type of measurement, the level of transcription of a gene whose transcription is dysregulated by mutant polyglutamine protein is a measurement of absolute level of transcription of a gene whose transcription is dysregulated by mutant polyglutamine protein. This could be expressed, for example, in terms of molecules per amount of tissue. Another measurement of the level of transcription of a gene whose transcription is dysregulated by a mutant polyglutamine protein is a measurement of the change over time in the level of transcription of the gene whose transcription dysregulated by mutant polyglutamine protein and/or a measurement of a change in the activity over time of the gene product. This may be expressed in an absolute amount or may be expressed in terms of a percentage increase or decrease over time. Yet another measurement of the level of transcription of the gene whose transcription is dysregulated by mutant polyglutamine protein can be determined by utilizing a reporter system that contains a transcription reporter region that indicates transcription of the gene.

Importantly, levels of gene transcription dysregulated by mutant polyglutamine protein are advantageously compared to controls according to the invention. The control may be a predetermined value, which can take a variety of forms. It can be a single value, such as a median or mean. It can be established based upon comparative groups, such as in groups having normal amounts of transcription of a gene whose transcription would be dysregulated by mutant polyglutamine protein (e.g. the amount in a normal cell with non-mutant polyglutamine protein). Other groups that can be used as a comparative group are groups having abnormal amounts of gene transcription that is dysregulated by mutant polyglutamine protein. Another example of comparative groups would be groups having a particular disease (e.g., Huntington's disease, DRPLA, etc.), condition or symptoms, and groups without the disease, condition or symptoms. Another comparative group would be a group with a family history of a condition and a group without such a family history. The predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk the highest quadrant or quintile being individuals with the highest risk.

The predetermined value of course, will depend upon the particular population selected. For example, an apparently healthy population will have a different 'normal' range than will a population that is known to have a condition related to a mutant polyglutamine protein. Accordingly, the predetermined value selected may take into account the category in which an individual falls. Appropriate ranges and categories can be selected with no more than routine experimentation by those of ordinary skill in the art. By abnormally high it is meant high relative to a selected control. Typically the control will be based on apparently healthy normal individuals in an appropriate age bracket. As used herein, the term "difference" or "differences" means statistically significant difference or differences.

It will also be understood that the controls according to the invention may be, in addition to predetermined values, samples of materials tested in parallel with the experimental materials. Examples include samples from control populations or control samples generated through manufacture to be tested in parallel with the experimental samples.

The various assays used to determine the level of transcription of a gene whose transcription is dysregulated by mutant polyglutamine protein include: assays, such as described in the Examples section herein, and assays such as using materials that specifically bind to a product of the gene transcription; gel electrophoresis; NMR; and the like. Immunoassays may be used according to the invention including sandwich-type assays, competitive binding assays, one-step direct tests and two-step tests such as routinely practiced by those of ordinary skill in the art.

As mentioned above, it is also possible to characterize the existence of a polyglutamine expansion-associated disorder by monitoring changes in the absolute or relative level or amount of transcription of a gene whose transcription is dysregulated by a mutant polyglutamine protein over time. For example, in diseases in which dysregulation results in the reduction of transcription of one or more genes, it is expected that a decrease in the level of transcription of a gene whose transcription is dysregulated by a mutant polyglutamine protein may correlate with increasing severity of the polyglutamine expansion-associated disease. Similarly, in diseases in which dysregulation results in the enhancement (increase) in the level of transcription of one or more genes, it is expected that an increase in the level of transcription of a gene whose transcription is dysregulated by a mutant polyglutamine protein may correlate with increasing severity of the polyglutamine expansion-associated disease.

In addition, it will be understood that in diseases in which dysregulation results in the reduction of transcription of one or more genes it is expected that an increase in the level of transcription of a gene whose transcription is dysregulated by a mutant polyglutamine protein may correlate with decreasing severity of the polyglutamine expansion-associated disease. Similarly, in diseases in which dysregulation results in the enhancement (increase) in the level of transcription of one or more genes, it is expected that a decrease in the level of transcription of a gene whose transcription is dysregulated by a mutant polyglutamine protein may correlate with decreasing severity of the polyglutamine expansion-associated disease.

Accordingly, one can monitor the level of transcription of a gene whose transcription is dysregulated by a mutant polyglutamine protein to determine if the status (e.g. stage, severity, etc.) of a polyglutamine expansion-associated disease of a subject is changing. Changes in relative or absolute level of transcription of a gene whose transcription is dysregulated by a mutant polyglutamine protein of greater than 0.1% relative to a normal control level may indicate an abnormality. Preferably, the change in level of transcription of a gene whose transcription is dysregulated by a mutant polyglutamine protein, which indicates an abnormality, is greater than 0.2%, greater than 0.5%, greater than 1.0%, 2.0%, 3.0%, 4.0%, 5.0%, 7.0%, 10%,. 15%, 20%, 25%, 30%, 40%, 50%, or more. Other changes, (e.g. increases or reductions) in levels of transcription of a gene whose transcription is dysregulated by a mutant polyglutamine protein over time may indicate an onset, progression, regression, or remission of the polyglutamine expansion-associated disease in the subject. As described above, in some disorders an increase in the level of transcription of a gene whose transcription is dysregulated by a mutant polyglutamine protein may mean regression of the disorder. Such a regression may be associated with a clinical treatment of the disorder. Thus, the methods of the invention can be used to determine the efficacy of a therapy for a polyglutamine expansion-associated disease (e.g. Huntington's disease). In some disorders a decrease in level of transcription of one or more genes that is dysregulated by a mutant polyglutamine protein may mean progression or onset of the disorder. It will be understood that in other disorders (e.g. where dysregulation results in an increase in transcription) a decrease in level of transcription of one or more genes dysregulated by a mutant polyglutamine protein may mean regression of the disorder. Such a regression may be associated with a clinical treatment of the disorder thus the methods of the invention can be used to determine the efficacy of a therapy for a polyglutamine expansion-associated disease. In some disorders an increase in the level of transcription of one or more genes dysregulated by a mutant polyglutamine protein may mean progression or onset of the disorder.

The invention in another aspect provides a diagnostic method to determine the effectiveness of treatments for abnormal levels of gene transcription dysregulated by a mutant polyglutamine protein. The "evaluation of treatment" as used herein, means the comparison of a subject's levels of gene transcription dysregulated by a mutant polyglutamine protein measured in samples collected from the subject at different sample times, preferably at least one day apart. In some embodiments, the time to obtain the second sample from the subject is at least one day after obtaining the first sample, which means the second sample is obtained at any time following the day of the first sample collection, preferably at least 12, 18, 24, 36, 48 or more hours after the time of first sample collection. In some embodiments, the second sample is obtained from the subject 1, 2, 3, 4, 5, 6, 7 8, 9, 10, 11, or more hours after the first sample is obtained. It will be understood that the multiple samples may also be obtained from cells and/or tissues in culture, thus the invention includes methods of testing treatments in vitro in addition to the methods for testing treatments and their effects in vivo.

The comparison of the level of transcription of a gene whose transcription is dysregulated by a mutant polyglutamine protein in two or more samples, taken at different times or on different days, is a measure of level of the subject's (or tissue's and/or cell's) diagnostic status for a polyglutamine expansion-associated disease and allows evaluation of a treatment to regulate the level of transcription of a gene whose transcription is dysregulated by a mutant polyglutamine protein. The comparison of a subject's, tissue's, and/or cell's level of transcription of a gene whose transcription is dysregulated by a mutant polyglutamine protein measured in samples obtained on different days provides a measure of the status of the polyglutamine expansion-associated disease to determine the effectiveness of any treatment to regulate the level of gene transcription dysregulated by a mutant polyglutamine protein in the subject, tissue, and/or cell.

As will be appreciated by those of ordinary skill in the art, the evaluation of a treatment also may be based upon an evaluation of the symptoms or clinical end-points of the associated disease. In some instances, the subjects to which the methods of the invention are applied are already diagnosed as having a particular condition or disease. In other instances, the measurement will represent the diagnosis of the condition or disease. In some instances, the subjects will already be undergoing drug therapy for a polyglutamine expansion-associated disease (e.g. Huntington's disease, DRPLA, etc.), while in other instances the subjects will be without present drug therapy for a polyglutamine expansion-associated disease.

Agents, e.g. antibodies and/or antigen-binding fragments thereof, that specifically bind to the product of a gene whose transcription is dysregulated by a mutant polyglutamine protein, or that specifically bind to other transcription-associated proteins, are useful in additional diagnostic methods. As described herein, the antibodies of the present invention may be prepared by any of a variety of methods, including administering protein, fragments of protein, cells expressing the protein or fragments thereof and the like to an animal to induce polyclonal antibodies. The production of monoclonal antibodies is well known in the art. As detailed herein, such antibodies or antigen-binding fragments thereof may be used for example to identify tissues expressing protein or to purify protein.

As detailed herein, the foregoing antibodies or antigen-binding fragments thereof and other binding molecules may be used for example to identify a product of a gene whose transcription is dysregulated by a mutant polyglutamine protein, or that specifically bind to other transcription-associated proteins. Antibodies also may be coupled to specific diagnostic labeling agents for imaging of cells and tissues with an abnormal level of transcription of a gene whose transcription is dysregulated by a mutant polyglutamine protein; or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99 m, iodine-131 and indium-111, nuclides for nuclear magnetic resonance such as fluorine and gadolinium. Other diagnostic agents useful in the invention will be apparent to one of ordinary skill in the art.

Using methods described herein and/or methods that are well known in the art, agents (e.g., antibodies or antigen-binding fragments thereof) can be identified and utilized that bind specifically to product of a gene whose transcription is dysregulated by a mutant polyglutamine protein, or that specifically bind to another transcription-associated protein that is associated with a polyglutamine expansion disease. As used herein, "binding specifically to" means capable of distinguishing the identified material from other materials sufficient for the purpose to which the invention relates. Thus, "binding specifically to" a product of a gene whose transcription is dysregulated by a mutant polyglutamine protein, or to another transcription-associated protein means the ability to bind to and distinguish such proteins from other proteins. In some embodiments, an agent of the invention may bind specifically to a complex that includes one or more polypeptides that are associated with transcription of a gene whose transcription is dysregulated by a mutant polyglutamine protein, for example a complex that includes Sp1 and/or TAFII130 protein.

The invention also provides agents (e.g. antibodies) for use in methods to modulate the level of transcription of a gene whose transcription is dysregulated by a mutant polyglutamine protein. In such methods, the antibodies recognize and bind specifically to a protein, a fragment thereof, and/or a complex of proteins that is associated with transcription of a gene whose transcription is dysregulated by a mutant polyglutamine protein. The binding of the antibody enhances or inhibits transcription of the gene. Methods to modulate (increase or decrease) the level of transcription the gene may be used to treat a polyglutamine expansion-associated disease, for example, methods utilizing agents (e.g. antibodies) to increase transcription by Sp1 and/or TAFII130, may be used to prevent or treat Huntington's disease.

Agents that bind to a protein or fragment thereof that is associated with a gene whose transcription is dysregulated by a mutant polyglutamine protein include polypeptide agents. Such polypeptides include polyclonal and monoclonal antibodies, prepared according to conventional methodology. Antibodies that bind a protein or fragment thereof that is associated with gene whose transcription is dysregulated by a mutant polyglutamine protein are useful for determining the presence, absence, or amount of the protein, (e.g. in a assay and/or a cell or tissue sample). Such antibodies include, but are not limited to: antibodies that bind specifically to a protein that is associated with a gene whose transcription is dysregulated by a mutant polyglutamine protein, antibodies that bind specifically to fragments of a protein that is associated with a gene whose transcription is dysregulated by a mutant polyglutamine protein, and antibodies that bind to complexes of proteins or fragments thereof that are associated with a gene whose transcription is dysregulated by a mutant polyglutamine protein. Certain antibodies useful in the methods of the invention already are known in the art and include for example, the antibodies provided in the Examples section herein.

Significantly, as is well-known in the art, only a small portion of an antibody molecule, the paratope, is involved in the binding of the antibody to its epitope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F9(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (Frs), which maintain the tertiary structure of the paratope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')$_2$, Fab, Fv and Fd fragments; chimeric antibodies in which the Fc and/or Fr and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention involves in part, polypeptides of numerous sizes and types that bind specifically to a protein or fragment thereof or a complex of proteins or fragments thereof, that is associated with transcription of a gene whose transcription is dysregulated by a mutant polyglutamine protein. These polypeptides may be derived also from sources other than antibody technology. For example, such polypeptide-binding agents can be provided by degenerate peptide libraries, which can be readily prepared in solution, in immobilized form or as phage display libraries. Combinatorial libraries also can be synthesized of peptides containing one or more amino acids. Libraries further can be synthesized of peptoids and non-peptide synthetic moieties.

The invention also relates in some aspects to methods to identify pharmacological agents that modulate the dysregulation of genes by a mutant polyglutamine protein. A wide variety of assays to identify pharmacological agents that modulate gene transcription dysregulated by mutant polyglutamine protein and/or modulate the stability of a gene transcription-associated protein or protein complex that is associated with gene transcription dysregulated by a mutant polyglutamine protein, can be used in accordance with the aspects of the invention, including, labeled in vitro protein-protein binding assays, electrophoretic mobility shift assays, immunoassays, cell-based assays such as two- or three-hybrid screens, transcription assays, expression assays, etc. The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents encompass numerous chemical classes, although typically they are organic compounds. In some embodiments, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with proteins and/or nucleic acid molecules, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid molecule, the agent typically is a DNA or RNA molecule, although modified nucleic acid molecules as defined herein are also contemplated.

It is contemplated that cell-based assays as described herein can be performed using cell samples and/or cultured cells. Cells include cells transformed to express a protein or polypeptide encoded by a gene whose transcription is dysregulated by mutant polyglutamine protein, and cells treated using methods described herein to modulate (e.g. inhibit or enhance) the level of transcription of a gene whose transcription is dysregulated by mutant polyglutamine protein.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

An assay may be used to identify candidate agents that directly or indirectly modulate the mediation of gene transcription by mutant polyglutamine protein. In general, the mixture of the foregoing assay materials is incubated under conditions whereby, but for the presence of the candidate pharmacological agent, modulation (e.g. enhancement or inhibition) of the gene transcription occurs. For example, such an assay may indicate an candidate agent is useful as a therapeutic in Huntington's disease if in the assay, the presence of the candidate pharmacological agent prevents the mutant huntingtin protein from inhibiting and/or disrupting Sp1 and/or TAFII130 activity. It will be understood that a candidate pharmacological agent that is identified as a modulating agent may be identified as reducing or eliminating the dysregulation of transcription by a mutant polyglutamine protein. A reduction in dysregulation need not be the absence of all dysregulation, but may be a lower level of dysregulation.

The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of transcription products of a gene whose transcription dysregulated by a mutant polyglutamine protein is detected by any convenient method available to the user.

The invention also relates in part to the use of methods and/or compounds to prevent and/or treat polyglutamine expansion-associated disorders and/or manifestations of polyglutamine-associated disorders. Compounds for the prevention and/or treatment of polyglutamine expansion-associated disorders include compounds that modulate the dysregulation of gene transcription by mutant polyglutamine proteins. The repression or enhancement of gene transcription by a mutant polyglutamine protein may be modulated using methods and/or compounds that modulate the gene transcription either directly or indirectly. For example the compounds may modulate the transcription of the genes directly or may modify the stability and/or activity of polypeptides or proteins that are accessories to the transcription of the gene whose transcription is dysregulated by a polyglutamine protein.

As used herein, the term "modulate" means to change, which in some embodiments means to enhance and in other embodiments, means to inhibit. In some embodiments, transcription of a gene whose transcription is dysregulated by a polyglutamine protein is enhanced. In some embodiments, stabilization or activity of one or more proteins or polypeptides that are involved in the transcription of a gene whose transcription is dysregulated by a mutant polyglutamine protein is enhanced or increased. It will be understood that increase may mean an increase to any level that is significantly greater than the original level or a control level. In certain embodiments, transcription of a gene whose transcription is dysregulated by a polyglutamine protein is inhibited. In some embodiments, stabilization or activity of one or more proteins or polypeptides that are involved in the transcription of a gene whose transcription is dysregulated by a mutant polyglutamine protein is inhibited or decreased. It will be understood that decrease may mean a decrease to any level that is significantly less than the original level or a control level.

The molecules of the invention that modulate the dysregulation of gene transcription by a mutant polyglutamine protein may include small molecules, polypeptides, (for example, competitive ligands and antibodies, or antigen-binding fragments thereof), and nucleic acids. For example, compositions of the invention may include nucleic acids that encode a molecule that acts to increase transcription of a gene whose transcription is dysregulated by a mutant polyglutamine protein. For example, a composition of the invention for treating or preventing Huntington's disease may include a molecule that increases the level and/or activity of Sp1 and/or TAFII130 protein, fragments, and/or complexes thereof. For example, compositions of the invention may include a nucleic acid molecule that encodes Sp1 or TAFII130, or a fragment thereof. In other embodiments, a composition of the invention may include a molecule that acts to increase the level and/or activity of Sp1 or TAFII130, or a fragment thereof. In some embodiments, a fragment of a protein may be a functional fragments. A functional fragment is a fragment of a protein that maintains all or part of the normal function of the full protein. Compositions of the invention also may include polypeptides that increase the transcription of a gene whose transcription is modified by a mutant polyglutamine protein. Such polypeptides include, but are not limited to antibodies or antigen-binding fragments thereof.

In some embodiments the methods and compositions of the invention are useful to make and/or test animal or cell models of polyglutamine expansion-associated diseases. For example, it may be desirable to use methods and/or compositions of the invention to increase the repression of transcription of a gene whose transcription is dysregulated by a mutant polyglutamine protein. The level of transcriptional repression by a mutant polyglutamine protein may be increased using methods to 1) decrease the level of transcription of a gene whose transcription is dysregulated by a mutant polyglutamine protein or 2) to decrease the level, stabilization, and/or activity of a protein that is associated with the transcription of a gene dysregulated by a mutant polyglutamine protein. For example, methods of the invention include 1) the administration of molecules that are antisense of a nucleic acid that encodes a protein that is associated with transcription of a gene whose transcription is dysregulated by a mutant polyglutamine protein (e.g. antisense of the nucleic acids that encode Sp1 and/or TAFII130) 2) RNAi and/or siRNA inhibition methods, and/or 3) administration of antibodies that block the functional activity of the proteins associated with the transcription of a gene that is dysregulated by a mutant polyglutamine protein. (e.g. antibodies that block the activity of Sp1 and/or TAFII130 proteins or complexes that include a Sp1 and/or TAFII130 protein). The methods of increasing the repression of transcription of a gene whose transcription is dysregulated by a mutant polyglutamine protein may also include administering polypeptides or nucleic acids that encode polypeptides that are variants of proteins involved in the transcription of the gene but are not fully functional. Such dominant negative variants may compete with the functional endogenous versions in a cell, tissue, or subject, and thereby increase the repression of the transcription of a gene whose transcription is dysregulated by a mutant polyglutamine protein. The compounds of the invention that increase the repression of the transcription of a gene whose transcription is dysregulated by a mutant polyglutamine protein, which include for example, antisense oligonucleotides, RNAi and/or siRNA oligonucleotides, antibodies, nucleic acids, an/or polypeptides may be administered as part of a pharmaceutical composition.

It will be understood that for diseases in which the dysregulation includes an increase in the transcription of a gene whose transcription is dysregulated by a mutant polyglutamine protein, an animal or cell model may be produced by using the methods and/or compositions of the invention to increase transcription of the gene. In addition, one of ordinary skill in the art will recognize that for diseases in which the dysregulation results in a decrease in the transcription of a gene whose transcription is dysregulated by a mutant polyglutamine protein, an animal or cell model may also be produced by using the methods and/or compositions of the invention to decrease transcription of the gene.

One set of embodiments of the aforementioned compositions that inhibit repression of transcription by a mutant polyglutamine proteins in a polyglutamine expansion-associated disorder molecules include nucleic acid molecules that reduce expression of genes via antisense or RNA interference (RNAi or siRNA). One example of the use of antisense, RNAi or siRNA in the methods of the invention, although not intended to be limiting, is their use to decrease the level of expression of an accessory protein, examples of which include Sp1 and/or TAFII130. The antisense oligonucleotides, RNAi, or siRNA nucleic acid molecules used for this purpose may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art-recognized methods, which may be carried out manually or by an automated synthesizer. They also may be produced recombinantly by vectors.

In some embodiments of the invention, the antisense, RNAi, and/or siRNA oligonucleotides also may include "modified" oligonucleotides. That is, the oligonucleotides may be modified in a number of ways, which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars that are covalently attached to low molecular weight organic groups other than a hydroxyl group at the 3' position and other than a phosphate group at the 5' position. Thus, modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acid molecules encoding proteins of the invention, together with pharmaceutically acceptable carriers.

The methods to modulate the dysregulation of gene transcription in polyglutamine expansion-associated diseases also include methods to increase expression of proteins or fragments or variants of proteins that enhance transcription of a gene whose transcription is dysregulated by a mutant polyglutamine protein. Thus, the invention includes methods that increase the stability, activity, or function of a protein associated with inhibiting the dysregulation of gene transcription in polyglutamine expansion-associated diseases. Thus, it will be recognized that the invention embraces the use of sequences that encode a protein or fragment or variant thereof, in expression vectors, as well their use to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as human, mouse, hamster, pig, goat, primate, etc. They may be of a wide variety of tissue types, and they may be primary cells or cell lines. The expression vectors require that the pertinent sequence, i.e., those nucleic acids described supra, be operably linked to a promoter.

The invention also permits the construction of polypeptide gene "knock-outs" or "knock-ins" in cells and in animals, providing materials for studying certain aspects of disorders associated with a polyglutamine expansion. For example, a knock-out mouse may be constructed and examined for clinical parallels between the model and characteristics and symptoms found in subjects with a polyglutamine expansion-associated disease, e.g. Huntington's disease. It will be understood that some polyglutamine expansion-associated disease models will be characterized by an increase in dysregulation of transcription of a protein whose transcription is dysregulated by a mutant polyglutamine protein and other polyglutamine-expansion associated disease models will be characterized by a decrease in the dysregulation of transcription of a protein whose transcription is dysregulated by a mutant polyglutamine protein. Thus, animal or cell models for some diseases may be constructed in which the level, stability, activity and/or function of a protein associated with transcription of a gene whose transcription is dysregulated by a mutant polyglutamine protein is decreased and animal and/or cell models for other diseases may be constructed in which the level stability, activity and/or function of a protein associated with transcription of a gene whose transcription is dysregulated by a mutant polyglutamine protein is increased. Such a cellular or animal model may be useful for assessing treatment strategies for polyglutamine expansion-associated diseases, e.g., Huntington's disease. This type of knock-out model provides a model with which to evaluate the effects of candidate pharmacological agents (e.g. enhancing effects) on a living animal that has an abnormal level of transcription of a gene whose transcription is dysregulated by a mutant polyglutamine protein.

According to another aspect of the invention, a transgenic non-human animal comprising an expression vector of the invention is provided, including a transgenic non-human animal which has altered expression of a protein associated with transcription of a gene whose transcription is dysregulated by a mutant polyglutamine protein, for example altered expression of transcription factors, e.g. Sp1 and/or TAFII130 protein and/or altered activity of Sp1 and/or TAFII130.

As used herein, "transgenic non-human animals" includes non-human animals having one or more exogenous nucleic acid molecules incorporated in germ line cells and/or somatic cells. Thus the transgenic animal include knock-out animals having a homozygous or heterozygous gene disruption by homologous recombination, animals having episomal or chromosomally incorporated expression vectors, etc. Knock-out animals can be prepared by homologous recombination using embryonic stem cells as is well known in the art. The recombination can be facilitated by the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to nucleic acid molecules of the invention to increase or decrease expression of the encoded polypeptide molecule in a regulated or conditional manner. Trans-acting negative or positive regulators of polypeptide activity or expression also can be operably linked to a conditional promoter as described above. Such trans-acting regulators include antisense nucleic acid molecules, nucleic acid molecules that encode dominant negative molecules, transcription factors, ribozyme molecules specific for nucleic acid molecules, and the like. The transgenic non-human animals are useful in experiments directed toward testing biochemical or physiological effects of diagnostics or therapeutics for conditions characterized by increased or decreased levels of a protein associated with transcription of a gene whose transcription is dysregulated by a mutant polyglutamine protein, for example Sp1 and/or TAFII130 protein. Other uses will be apparent to one of ordinary skill in the art.

The prevention and treatment methods of the invention include administration of compounds that modulate the transcription dysregulation by mutant polyglutamine proteins. Various techniques may be employed for introducing dysregulation-modulating compounds of the invention to cells, depending on whether the compounds are introduced in vitro or in vivo in a host. In some embodiments, the dysregulation-modulating compounds target a specific cell or tissue type, e.g. neuronal cells and/or tissues. Thus, the dysregulation-modulating compounds can be specifically targeted to neuronal tissue (e.g., neuronal cells) using various delivery methods, including, but not limited to: administration to neuronal tissue, the addition of targeting molecules to direct the compounds of the invention to neuronal cells and/or tissues. Additional methods to specifically target molecules and compositions of the invention to brain tissue and/or neuronal tissues are known to those of ordinary skill in the art.

In some embodiments of the invention, a dysregulation-modulating compound of the invention may be delivered in the form of a delivery complex. The delivery complex may deliver the dysregulation-modulating compound into any cell type, or may be associated with a molecule for targeting a specific cell type. Examples of delivery complexes include a dysregulation-modulating compound of the invention associated with: a sterol (e.g., cholesterol), a lipid (e.g., a cationic lipid, virosome or liposome), or a target cell specific binding agent (e.g., an antibody, including but not limited to monoclonal antibodies, or a ligand recognized by target cell specific receptor). Some delivery complexes may be sufficiently stable in vivo to prevent significant uncoupling prior to internalization by the target cell. However, the delivery complex can be cleavable under appropriate conditions within the cell so that the dysregulation-modulating compound is released in a functional form.

An example of a targeting method is the use of liposomes to deliver a dysregulation-modulating compound of the invention into a cell. Liposomes may be targeted to a particular tissue, such as neuronal cells, by coupling the liposome to a specific ligand such as a monoclonal antibody, sugar, glycolipid, or protein. Such proteins include proteins or fragments thereof specific for a particular cell type, antibodies for proteins that undergo internalization in cycling, proteins that target intracellular localization and enhance intracellular half life, and the like.

Liposomes are commercially available from Invitrogen, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications.

When administered, the dysregulation-modulating compounds (also referred to herein as therapeutic compounds and/or phannaceutical compounds) of the present invention are administered in pharmaceutically acceptable preparations. Such preparations may routinely contain pharmaceutically acceptable concentrations of salt, buffering agents, preservatives, compatible carriers, and optionally other therapeutic agents.

The invention provides a composition of the above-described agents for use as a medicament, methods for preparing the medicament and methods for the sustained release of the medicament in vivo. Delivery systems can include time-release, delayed release or sustained release delivery systems. Such systems can avoid repeated administrations of the therapeutic agent of the invention, increasing convenience to the subject and the physician. Many types of release delivery systems are available and known to those of ordinary skill in the art. They include polymer-based systems such as polylactic and polyglycolic acid, poly(lactide-glycolide), copolyoxalates, polyanhydrides, polyesteramides, polyorthoesters, polyhydroxybutyric acid, and polycaprolactone. Microcapsules of the foregoing polymers containing drugs are described in, for example, U.S. Pat. No. 5,075,109. Nonpolymer systems that are lipids including sterols such as cholesterol, cholesterol esters and fatty acids or neutral fats such as mono-, di- and tri-glycerides; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In one particular embodiment, the preferred vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System". PCT/US/03307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the compound(s) of the invention is encapsulated or dispersed within the biocompatible, preferably biodegradable polymeric matrix disclosed in PCT/US/03307. The polymeric matrix preferably is in the form of a microparticle such as a microsphere (wherein the compound is dispersed throughout a solid polymeric matrix) or a microcapsule (wherein the compound is stored in the core of a polymeric shell). Other forms of the polymeric matrix for containing the compounds of the invention include films, coatings, gels, implants, and stents. The size and composition of the polymeric matrix device is selected to result in favorable release kinetics in the tissue into which the matrix device is implanted. The size of the polymeric matrix device further is selected according to the method of delivery that is to be used. The polymeric matrix composition can be selected to have both favorable degradation rates and also to be formed of a material that is bioadhesive, to further increase the effectiveness of transfer when the device is administered. The matrix composition also can be selected not to degrade, but rather, to release by diffusion over an extended period of time.

Both non-biodegradable and biodegradable polymeric matrices can be used to deliver agents of the invention of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the agents of the invention are delivered using the bioerodible implant by way of diffusion, or more preferably, by degradation of the polymeric matrix. Exemplary synthetic polymers that can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581–587, the teachings of which are incorporated herein by reference, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Use of a long-term sustained release implant may be particularly suitable for treatment of established neurological disorder conditions as well as subjects at risk of developing a neurological disorder. "Long-term" release, as used herein, means that the implant is constructed and arranged to deliver therapeutic levels of the active ingredient for at least 7 days, preferably 30–60 days, and more preferably several months or years. The implant may be positioned at or near the site of the neurological damage or the area of the brain or nervous system affected by or involved in the neurological disorder. Long-term sustained release implants are well known to those of ordinary skill in the art and include some of the release systems described above.

Some embodiments of the invention include methods for treating a subject to reduce the risk of manifesting a disorder associated with abnormal levels of transcription of gene whose transcription is dysregulated by a mutant polyglutamine protein. The methods involve selecting and administering to a subject who is known to have, is suspected of having, or is at risk of having an abnormal level of transcription of a gene whose transcription is dysregulated by a mutant polyglutamine protein, a dysregulation-modulating compound for treating the disorder. Preferably, the dysregulation-modulating compound is a compound for modulating (e.g. inhibiting or enhancing) levels of transcription of a gene whose transcription is dysregulated by a mutant polyglutamine protein and is administered in an amount effective to modulate (increase or decrease) levels of transcription of the gene.

Another aspect of the invention involves reducing the risk of manifesting a disorder associated with dysregulation of a gene whose transcription is dysregulated by a mutant polyglutamine protein using treatments and/or medications to modulate levels of a protein encoded by the dysregulated gene, therein reducing, for example, the subject's risk of a polyglutamine expansion-associated disease.

In a subject determined to have a polyglutamine expansion-associated disease, an effective amount of a dysregulation-modulating compound is that amount effective to modulate (e.g. increase of decrease) levels of repression of transcription of a gene whose transcription is dysregulated by a mutant polyglutamine protein. For example, in the case of Huntington's disease an effective amount may be an amount that increases (enhances) the level and/or activity of Sp1 and/or TAFII130 protein, in the subject. In instances in which dysregulation results in the increase of transcription of a protein, an effective amount may be an amount that deceases (inhibits) the level and/or activity of Sp1 and /or TAFII130 protein.

A response to a prophylatic and/or treatment method of the invention can, for example, also be measured by determining the physiological effects of the treatment or medication, such as the decrease or lack of disease symptoms following administration of the treatment or pharmacological agent. Other assays will be known to one of ordinary skill in the art and can be employed for measuring the level of the response. For example, the behavioral and neurological diagnostic methods that are used to ascertain the likelihood that a subject has a polyglutamine expansion-associated disease, e.g. Huntington's disease, DRPLA, etc, and to determine the putative stage of the disease can be used to ascertain the level of response to a prophylactic and/or treatment method of the invention. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount can depend upon the degree to which an individual has reduced (or enhanced) transcription of a gene whose transcription is dysregulated by a mutant polyglutamine protein.

The factors involved in determining an effective amount are well known to those of ordinary skill in the art and can be addressed with no more than routine experimentation. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

The therapeutically effective amount of a pharmacological agent of the invention is that amount effective to modulate the transcription of a gene whose transcription is dysregulated by a mutant polyglutamine protein and reduce, prevent, or eliminate the polyglutamine expansion-associated disorder and/or its symptoms. For example, testing can be performed to determine the level of transcription of a gene whose transcription is dysregulated by a mutant polyglutamine protein in a subject's tissue and/or cells. Additional tests useful for monitoring the onset, progression, and/or remission of polyglutamine expansion-associated diseases such as those described above herein, are well known to those of ordinary skill in the art. As would be understood by one of ordinary skill, for some disorders (e.g. Huntington's disease, DRPLA, etc.) an effective amount would be the amount of a pharmacological agent of the invention that increases the transcription of a gene whose transcription is dysregulated by a mutant polyglutamine protein to a level that diminishes the disease, as determined by the aforementioned tests.

In the case of treating a particular disease or condition the desired response is inhibiting the progression of the disease or condition. This may involve only slowing the progression of the disease temporarily, although more preferably, it involves halting the progression of the disease permanently. This can be monitored by routine diagnostic methods known to one of ordinary skill in the art for any particular disease. The desired response to treatment of the disease or condition also can be delaying the onset or even preventing the onset of the disease or condition.

The pharmaceutical compositions used in the foregoing methods preferably are sterile and contain an effective amount of a pharmacological agent for producing the desired response in a unit of weight or volume suitable for administration to a patient. The doses of pharmacological agents administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of a pharmacological agent of the invention may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

Various modes of administration will be known to one of ordinary skill in the art which effectively deliver the pharmacological agents of the invention to a desired tissue, cell, or bodily fluid. The administration methods include: topical, intravenous, oral, inhalation, intracavity, intrathecal, intrasynovial, buccal, sublingual, intranasal, transdernal, intravitreal, subcutaneous, intramuscular and intradermal administration. The invention is not limited by the particular modes of administration disclosed herein. Standard references in the art (e.g., *Remington's Pharmaceutical Sciences*, 20th Edition, Lippincott, Williams and Wilkins, Baltimore Md., 2001) provide modes of administration and formulations for delivery of various pharmaceutical preparations and formulations in pharmaceutical carriers. Other protocols which are useful for the administration of pharmacological agents of the invention will be known to one of ordinary skill in the art, in which the dose amount, schedule of administration, sites of administration, mode of administration (e.g., intra-organ) and the like vary from those presented herein.

Administration of pharmacological agents of the invention to mammals other than humans, e.g. for testing purposes or veterinary therapeutic purposes, is carried out under substantially the same conditions as described above. It will be understood by one of ordinary skill in the art that this invention is applicable to both human and animal diseases including polyglutamine expansion-associated diseases of the invention. Thus, this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the pharmacological agents and/or compositions of the invention.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride; chlorobutanol; parabens and thimerosal. The pharmaceutical compositions may conveniently be presented in unit dosage form and may be prepared by any of the methods well known in the art of phannacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration may be formulated according to known methods using suitable dispersing or wetting agents and suspending agents. The sterile injectable preparation also may be a sterile injectable solution or suspension in a non-toxic parenterally acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

In general, the treatment methods involve administering an agent to modulate the level of transcription of a gene whose transcription is dysregulated by a mutant polyglutamine protein, and/or an agent to modulate the activity of a protein associated dysregulation of gene transcription dysregulated by a mutant polyglutamine protein. Thus, in certain embodiments, the treatment methods include gene therapy applications. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements, which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

In certain embodiments, the method for treating a subject with a disorder characterized by dysregulation of a gene whose transcription is dysregulated by a mutant polyglutamine protein involves administering to the subject an effective amount of a nucleic acid molecule to treat the disorder. In certain embodiments, the method for treatment involves administering to a subject an effective amount of a nucleic acid that encodes a protein associated with the transcription of a gene whose transcription is dysregulated by a mutant polyglutamine protein to treat the disorder. An exemplary protein to increase using a method of the invention, for increasing the transcription of a gene whose transcription is dysregulated by a mutant polyglutamine protein in Huntington's disease is Sp1 and/or TAFII130. In yet another embodiment, the treatment method involves administering to the subject an effective amount of a binding polypeptide (e.g antibody, or antigen-binding fragment thereof) to modulate binding between one or more proteins of the invention and, thereby treat the disorder. In some embodiments, the treatment method involves administering to the subject an effective amount of a binding polypeptide to enhance the level and/or activity of a protein associated with the transcription of a gene whose transcription is dysregulated by a mutant polyglutamine protein, to decrease dysregulation of a gene whose transcription is dysregulated by a mutant polyglutamine protein. In certain embodiments, the binding polypeptide is an antibody or an antigen-binding fragment thereof, more preferably, the antibodies or antigen-binding fragments are labeled with one or more cytotoxic agents.

According to yet another aspect of the invention, expression vectors comprising any of the isolated nucleic acid molecules of the invention, preferably operably linked to a promoter are provided. In a related aspect, host cells transformed or transfected with such expression vectors also are provided. Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a protein of the invention, fragment, or variant thereof. The heterologous DNA (RNA) is placed under operable control of transcriptional elements to permit the expression of the heterologous DNA in the host cell.

As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays known in the art (e.g., β-galactosidase or alkaline phosphatase), and genes that visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

In some embodiments, a virus vector for delivering a nucleic acid molecule encoding a protein associated with transcription of a gene whose transcription is dysregulated by a mutant polyglutamine protein (e.g. Sp1 and/or TAFII130), fragment thereof, antisense molecule, RNAi, or siRNA molecule of the invention, is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., *Virology* 219:220–227, 1996; Eloit et al., *J. Virol.* 7:5375–5381, 1997; Chengalvala et al., *Vaccine* 15:335–339, 1997), a modified retrovirus (Townsend et al., *J. Virol.* 71:3365–3374, 1997), a nonreplicating retrovirus (Irwin et al., *J. Virol.* 68:5036–5044, 1994), a replication defective Semliki Forest virus (Zhao et al., *Proc. Natl. Acad. Sci. USA* 92:3009–3013, 1995), canarypox virus and highly attenuated vaccinia virus derivative (Paoletti, *Proc. Natl. Acad. Sci. USA* 93:11349–11353, 1996), non-replicative vaccinia virus (Moss, *Proc. Natl. Acacl. Sci. USA* 93:11341–11348, 1996), replicative vaccinia virus (Moss, *Dev. Biol. Stand.* 82:55–63, 1994), Venzuelan equine encephalitis virus (Davis et al., *J. Virol.* 70:3781–3787, 1996), Sindbis virus (Pugachev et al., *Virology* 212:587–594, 1995), and Tyvirus-like particle (Allsopp et al., *Eur. J. Immunol* 26:1951–1959, 1996). In preferred embodiments, the virus vector is an adenovirus.

Another preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman Co., New York (1990) and Murry, E. J. Ed. "Methods in Molecular Biology," vol. 7, Humana Press, Inc., Cliffton, N.J. (1991).

Preferably the foregoing nucleic acid delivery vectors: (1) contain exogenous genetic material that can be transcribed and translated in a mammalian cell and that can suppress polyglutamrine expansion-associated disorders, and preferably (2) contain on a surface a ligand that selectively binds to a receptor on the surface of a target cell, such as a mammalian cell, and thereby gains entry to the target cell.

Various techniques may be employed for introducing nucleic acid molecules of the invention into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like.

For certain uses, it is preferred to target the nucleic acid molecule to particular cells. In such instances, a vehicle used for delivering a nucleic acid molecule of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid molecule delivery vehicle. Especially preferred are monoclonal antibodies. Where liposomes are employed to deliver the nucleic acid molecules of the invention, proteins that bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acid molecules into cells, as is known by those skilled in the art. Such systems even permit oral delivery of nucleic acid molecules.

In addition to delivery through the use of vectors, nucleic acids of the invention may be delivered to cells without vectors, e.g. as "naked" nucleic acid delivery using methods known to those of skill in the art.

The invention will be more fully understood by reference to the following examples. These examples, however, are merely intended to illustrate the embodiments of the invention and are not to be construed to limit the scope of the invention.

EXAMPLES

Example 1

Introduction

Huntington's disease (HD) is an inherited neurodegenerative disease caused by expansion of a polyglutamine tract in the huntingtin protein. We have identified that huntingtin interacts with the transcriptional activator Sp1 and coactivator TAFII130. Coexpressionof Sp1 and TAFII130 in cultured striatal cells from wild-type and HD transgenic mice reverses the transcriptional inhibition of the dopamine D2 receptor gene caused by mutant huntingtin, as well as protects neurons from huntingtin-induced cellular toxicity. Furthermore, soluble mutant huntingtin inhibits Sp1 binding to DNA in postmortem brain tissues of both presymptomatic and affected HD patients.

Materials and Methods

Yeast Two-Hybrid System

Bait and prey constructs were generated from PCR amplification of the respective cDNAs with incorporation of an EcoR1 site in the 5' end and BamH1 site in the 3' end to allow simple unidirectional cloning into the two-hybrid vector (D. Krainc et al., *J. Biol. Chem.* 273:26218, 1998). TAFII130 constructs were made as described (D. Saluja et al., *Mol. Cell. Biol.* 18:5734, 1998). These insertions were in-frame with the LexA DNA binding domain and a hemaglutinin tag of the pJG4–5 vector. All the constructs were verified by DNA sequencing for correct reading frame and orientation. All assays were performed in triplicates and protein expression verified by Western blotting using standard procedures. The ability of the LexA fusion to bind operator was confirmed by a repression assay. The two-hybrid screen assays were performed as described (D. Krainc et al., *J. Biol. Chem.* 273:26218, 1998).

Co-Precipitation Assays

Human HEK293 cells were transfected with expression vectors using FuGENE6 Transfection Reagent (Roche Applied Science, Indianapolis, Ind.) according to the manufacturer's instructions. Total amount of plasmid DNA in individual plates was adjusted using empty vector plasmid. Thirty six hours after transfection, cells were sonicated for 5 sec in lysis buffer (20 mM HEPES, pH 7.4, 150 mM NaCl, 5 mM EDTA, 1% sodium deoxycholate, 0.5 mM DTT, 0.2 mM PMSF, 10 mM NaF, 10 mM sodium pyrophosphate, 10 ug/ml leupeptin and 10 ug/ml aprotinin). Immunoprecipitations were performed with anti-huntingtin antibody (Chemicon International, Temecula, Calif., MAB2166) and protein G Agarose (Roche) followed by washing four times with RIPA (75 mM NaCl, 25 mM $Na_2SO_4$ 1 mM EDTA, 0.5% sodium deoxycholate, 0.5% TritonX-100) or ice-cold phosphate buffered saline (PBS). Immunoprecipitates or total lysates were separated on sodium dodecyl sulphate-polyacrylamide gel electrophoresis (SDS-PAGE) and subjected to immunoblotting with anti-huntingtin and anti-Flag (Sigma-Aldrich, St. Louis, Mo.) or anti-HA antibodies (TAFII130). For coimmunoprecipitation experiments in human brain, tissues were homogenized using a polytron (Brinkmann Instruments Inc, Westbury, N.Y.) in ice-cold TE buffer (10 mM Tris-HCl, 5 mM EDTA, pH 7.4) containing 320 mM sucrose and centrifuged at 15,000 rpm at 4° C. for 20 min. The pellet was solubilized by adding 1% sodium deoxycholate in 50 mM Tris-HCl, pH 9.0 followed by incubation at 36° C. for 30 min. A 1/10 volume of a buffer containing 1% Triton X-100, 50 mM Tris-HCl, pH 9.0 was then added and the preparation was dialyzed against binding buffer (50 mM Tris-HCl, pH 7.4, 0.1% Triton X-100) overnight at 4° C. The sample was centrifuged at 37,000×g at 4° C. for 40 min. The supernatant was used for immunoprecipitation. Precoupling of antibodies to Protein A Sepharose beads and immunoprecipitation procedures were performed as previously described (A. W. Dunah et al., *Mol. Pharmacol.* 53:429, 1998). SDS-PAGE and the transfer of proteins to nitrocellulose were performed according to standard protocols. Samples were analyzed by SDS-PAGE, immunoblotted, and probed with anti-Sp1 antibody (Santa Cruz Biotechnology, Inc. Santa Cruz, Calif., sc-59) and anti-huntingtin antibody (Chemicon, MAB2166). The same blot was probed with anti-cadherin (cell adhesion molecule) antibody as a control for nonspecific interaction. The concentration of antibodies used for the immunoblots was 1–2 µg/ml. Experiments were performed with postmortem HD brains from presymptomatic patients, as well as affected HD patients. Age-matched control brains were used in each experiment.

Eletrophoretic Mobility Shift Assays

Human brain tissue Grades 1–4 according to Vonsattel classification (J. P. Vonsattel, et al., *J. Neuropathol. Exp. Neurol.* 44:559, 1985) from HD patients and age-matched controls originated from the Brain Bank at McLean Hospital in Boston, MA, from the Vonsattel lab and from our labs. Two of the three donors of Grade 1 HD brains were presymptomatic and one of them is shown here. EMSA for cultured cells and frozen human tissue was performed as described (D. Krainc et al., *J. Biol. Chem.* 273:26218, 1998, D. K. Lahiri, Y. Ge, *Brain Res. Protoc.* 5:257, 2000), except for the modifications as below. Nuclear extracts were prepared from the caudate nucleus and hippocampus. These regions were selected because of their differential vulnerability in HD (J. P. Vonsattel, et al., *Neuropathol. Exp. Neurol.* 44:559, 1985). Frozen postmortem human brain tissue (0.2 g) was rinsed in PBS buffer and spun at 1,500×g for 5 min. NP-40 (0.5% final) was added and homogenization performed with pestle, followed by incubation for 15 min to lyse the cells, and microcentrifuged for 2 min. The nuclear pellet was resuspended in buffer C (20 mM HEPES, pH 7.9, 400 mM NaCl, 1 mM each of EDTA, DTT, EGTA and PMSF) and placed on a rotary shaker for 20 min, followed by centrifugation at 11,000×g for 5 min, and removal of the supernatant that contained soluble nuclear proteins. We obtained about 4 µg of nuclear protein per mg of frozen tissue. EMSA was performed with labeled D2 receptor promoter fragment containing Sp1 site (underlined) (5'-CAGGGTGAC<u>CCCGCCCC</u>CTCCTCC-3' SEQ ID NO:1) (S. Yajima, et al., *DNA Cell Biol.* 17:471, 1998). The protein-DNA complexes were resolved on a 4% native polyacrylamide gel in 0.25×TBE (44.5 mM Tris-HCl, 44.5 mM boric acid, 1 mM EDTA) and visualized by autoradiography. The slowest migrating complex was supershifted with Sp1 antibody. To determine the molecular weight of retarded Sp1 band, we UV cross-linked the proteins to the labeled DNA probe, separated the DNA-protein complexes on a native gel, cut out each shifted complex and the crosslinked proteins were run on a SDS-denaturing polyacrylamide gel. For reactions analyzing the binding of purified Sp1 (Promega Corp., Madison, Wis.; 1.5 footprinting unit per reaction) to labeled consensus Sp1 site (underlined) [Promega; 5'-ATTCGATCG<u>GGGCGGGG</u>CGAGC-3' (SEQ ID NO:2), 50000 cpm] EMSA was performed as in (D. Krainc et al., *J. Biol. Chem.* 273:26218, 1998) except that 5 mM DTT and 1 µg/ml poly(dI-dC) were used. GST-huntingtin fusions (0.2 µg/ul) were a gift of E. Wanker and were purified as described (J. S. Steffan et al., *Nature* 413:739, 2001). An approximate 1:1 ratio of purified proteins was used. Coomassie blue staining and Western blotting were used to examine the purified proteins.

Neuronal Transfections and Immunocytochemistry

Striatal neurons were prepared from embryonic (E 17–18) rats and transfected as previously described (D. Krainc et al., *J. Biol. Chem.* 273:26218, 1998; F. Saudou et al., *Cell* 95:55, 1998). Plates were coated overnight with 0.1 mg/ml poly-L-ornithine solution. The cells were incubated in 5% $CO_2$ for 1 hr with 3 ml of fresh DMEM (w/out added glutamine). DNA/calcium phosphate precipitate was prepared by mixing one volume of DNA in 250 mM $CaCl_2$ with an equal volume of 2×HeBS (274 mM NaCl, 10 mM KCl, 2.4 mM $Na_2HPO_4$, 15 mM D-glucose, 42 mM HEPES, pH 7.05). The precipitate was allowed to form for 25–30 min in the dark at room temperature before addition to the cultures. Six to eight µg of plasmid DNA were used for each 60-mm-diameter plate. 120 µl of the DNA/calcium phosphate precipitate was added drop-wise to each 60-mm-diameter dish and mixed gently. Plates were then returned to the 5% $CO_2$ incubator. The incubation was stopped after 15–25 min by aspirating the media. Cells were then washed three times with 3 ml of DMEM (without added glutamine). The saved conditioned medium was added back to each plate, and the cells were returned to the 5% $CO_2$ incubator at 37° C. Choline acetyl-transferase (CAT) assays were carried out using the CAT/enzyme-linked immunosorbent kit (Roche), and the results were normalized to β-galactosidase activity. Transfected neurons were scored for cell death as described (F. Saudou et al., Cell 95:55, 1998). Cells were stained with the DNA dye Hoechst 33258 (Hoechst A G, Frankfurt, Germany). Neurons were scored as dead if they stained positively with TUNEL and had pyknotic and fragmented nuclei. Equal expression of transfected DNAs was confirmed by Western blot analysis. For immunocytochemistry, cultured striatal neurons were transfected at DIV 8 (8 days after plating) with either huntingtin constructs alone or a combination of huntingtin, Sp1 and HA-tagged TAFII130, and double-labeled at DIV 10. Endogenous dopamine D2 receptor was stained with polyclonal D2 antibody (Santa Cruz, sc-9113). Other antibodies used included mouse monoclonal anti-huntingtin (Chemicon, MAB2166), anti-flag (against flag-huntingtin), and anti-HA. Neurons were fixed with ice-cold methanol for 5 min at −20° C., washed in PBS three times for 5 min at room temperature, and incubated with primary antibodies in staining buffer (GDB, 30 mM phosphate buffer, pH 7.4, containing 0.2% gelatin, 0.5% Triton X-100, and 0.8 M NaCl) overnight at 4° C. The cells were then washed three times in wash buffer (WB, 20 mM phosphate buffer, pH 7.4, 0.5 M NaCl) for 10 min at room temperature. After incubating the cells with secondary antibody in GDB for 1 hr at room temperature, they were washed sequentially in WB and PBS for 10 min at room temperature. Experiments were performed in triplicate. Confocal microscopy was used to visualize the cells.

Real-time PCR

Individual huntingtin-, TAFII130- and Sp1-transfected cells identified by immunostaining, as well as untransfected neurons were aspirated into glass microelectrodes by applying negative pressure under visual control (D. J. Surmeier, et al., J. Neurosci. 16:6579, 1996). After aspiration, the electrode was broken and the contents ejected into a thin-walled PCR tube. At least 10 cells were pooled together in each group for analysis of D2 receptor expression. Experiments were performed in triplicate. D2 receptor RNA was isolated with Picopure RNA Isolation Kit (Arcturus, Mountain View, Calif.), and levels analyzed by cDNA synthesis and PCR with SYBR Green dye (PE Biosystems, Applied Biosystems, Foster City, Cailf.). The thermal cycling program for all primer sets was 94° C. for 1 min, 58° C. for 1 min, and 72° C. for 1.5 min for 45 cycles. All primer sets had PCR efficiency above 90% at 58° C. Primers for the D2 cDNA were D2R1-5'-GCAGTCGAGCTTTCAGAGCC-3' (SEQ ID NO:3) and 5'-TCTGCGGCTCATCGTCTTAAG-3' (SEQ ID NO:4) (404 and 317 bp; GenBank accession M36831) (D. J. Surmeier, et al., J. Neurosci. 16:6579, 1996). The accumulation of fluorescent products was monitored by iCycler (Bio-Rad, Hercules, Calif.). PCR baseline subtracted threshold values were calculated for each amplicon. PCR products were verified by melting temperature profiles of final products and by sequencing of PCR reactions. All RNA values were normalized to β-actin whose mRNA expression was not changed in transfected neurons, as determined by real-time RT-PCR. Negative controls for contamination from extraneous and genomic DNA were run for every batch of neurons. To ensure that genomic DNA did not contribute to the PCR products, neurons were aspirated and processed in the normal manner, except that the reverse transcriptase was omitted. Contamination from extraneous sources was checked by replacing the cellular template with water. Both controls were consistently negative in these experiments.

Immunohistochemistry and Western Blots

Series of 50 µm sections were processed for immunohistochemistry. To reduce endogenous peroxidase activity and nonspecific antibody binding, sections were incubated in 3% hydrogen peroxide and then PBS containing 4% normal goat serum (NGS) followed by PBS rinses. Sections were incubated in 2% NGS/PBS containing the primary antibody and 50 µg/ml of biotin for 48–72 hr. Sections were incubated overnight in biotinylated goat anti-mouse secondary antibody (Vector) in PBS containing 2% NGS and in avidin-biotin complex (Vector ABC Elite, Vector Laboratories, Inc., Burlingame, Calif.) for 4 hr. Final development was done by incubation in 0.05% 3,3'-diaminobenzidine tetrahydrochloride (DAB, Sigma) and 0.01% hydrogen peroxide in 50 mM Tris buffer (pH 7.5) for 5–15 min. Specific controls included omission of the primary antibody to determine the amount of background generated from the detection assay and preabsorption with excess target proteins when available to demonstrate specificity. We used Sp1 antibody (Santa Cruz, sc-59) and EM48 antibody which recognizes the N-terminal portion of huntingtin (amino acids 1–256, excluding polyglutamine and polyproline repeat stretches) that selectively immunoreacts with aggregates in human tissue (C. A. Gutekunst et al., J. Neurosci. 19:2522, 1999). Western blots were performed as described (F. C. Nucifora et al., Science 291:2423, 2001). Tissues were homogenized in 10 volumes of 50 mM Tris (pH 7.5) and 1% Triton X-100. The homogenate was spun for 30 min at 150,000×g. The pellet was resuspended in 50 mM Tris (pH 7.5) with 2% SDS and boiled for 4 min. Samples were spun at 1,000×g for 2 min, and the supernatant assayed for protein concentration, and equal amounts of protein analyzed by SDS-PAGE and immunoblotting.

Results and Discussion

Using the yeast two-hybrid system, we found that both Sp1 and TAFII130 interact with full-length huntingtin (FIG. 1). The interactions between Sp1 and huntingtin were stronger in the presence of an expanded polyglutamine repeat (HttQ75) as compared to the nonexpanded repeat length (HttQ17) (FIG. 1A), whereas the interactions between TAFII130 and huntingtin were not significantly influenced by the polyglutamine tract length (FIG. 1B). Although the glutamine-rich regions of Sp1 (Sp1AB) and TAFII130 (TAFII130-M) were sufficient for their interaction with huntingtin, the presence of the COOH-terminal DNA binding domain of Sp1 or the conserved COOH-terminal domain of TAFII130 resulted in stronger interaction. Because $NH_2$-terminal fragments of mutant huntingtin can effectively induce cell death in both in vivo and in vitro models (L. Mangiarini, et al., Cell 87:493, 1996; J. K. Copper, et al., Hum. Mol. Genet. 7:783, 1998; D. Martindale, et al., Nature Genet. 18:150, 1998; S. H. Li and X. Y. Li, Hum. Mol. Genet. 7:777, 1998), we examined the interactions of Sp1 and TAFII130 with the 480-amino acid NH$_2$-terminal fragment of huntingtin. Compared with the full-length protein, NH$_2$-terminal fragments showed similar, polyglutamine length-dependent interactions with Sp1, whereas their interactions with TAFII130 were independent of polyglutamine length (FIGS. 1A and B). FIG. 1 illustrates that Huntingtin interacted with Sp1 and TAFII130 in vitro and in human HD brain tissue. FIG. 1A illustrates results of yeast two-hybrid experiments, as described above herein, performed with full-length (HttQ17 and HttQ75) or truncated huntingtin constructs (Htt480Q17 and Htt480Q68) as prey against bait plasmids containing full-length Sp1 or Sp1 lacking the DNA binding domain (Sp1AB, amino acids 83 through 621). The β-galactosidase (β-gal) activity is displayed for each interaction as a percentage of the interaction between normal huntingtin and full-length Sp1 (set to 100%). Values are expressed as means±SEM. FIG. 1B illustrates results of yeast two-hybrid experiments performed and analyzed as described for FIG. 1A. TAFII130 and its derivatives containing the NH$_2$-terminal domain (TAFII130-N, amino acids 1 through 297), the glutamine-rich domain (TAFII130-M, amino acids 270 through 700), or the COOH-terminal domain (TAFII130-C, amino acids 646 through 947) were used as baits.

FIG. 1C shows interaction between huntingtin and Sp1 in HEK 293T cells. Wild-type huntingtin (HttQ17), mutant huntingtin (HttQ75), and FLAG-tagged Sp1 were transfected, immunoprecipitated (IP) with anti-Htt, and blotted with anti-FLAG or anti-Htt, as described above herein. Sp1 expression is shown on a sample of lysate (10%) used for immunoprecipitation (Input). Expressed FLAG-Sp1 and huntingtin are indicated by arrows on the left. FIG. 1D shows that Huntingtin and Sp1 interact in human HD brain tissue. Total homogenate was prepared from the caudate of grade 1 human HD brain tissue and immunoprecipitated with anti-Sp1 (lane 2), anti-Htt (lane 3), or nonimmune rabbit immunoglobulins (IgG, lane 4). Lane 1 shows 10% of the input. Antibody to cadherin (Cad) was used as a control for nonspecific interaction. FIG. 1E shows that Huntingtin and TAFII130 interact in human HD brain tissue. Immunoprecipitations were performed as in FIG. 1D, except that anti-TAFII130 was used (lane 2) (See Methods section). FIG. 1F shows reduced Sp1-TAFII130 interaction detected in human HD brain tissue. In these experiments, immunoprecipitations were performed as in FIG. 1D, except that anti-Sp1 (lanes 2 and 6) and anti-TAFII130 (lanes 3 and 7) were used for immunoprecipitations. A decrease in coprecipitated TAFII130 (upper panel, compare lanes 2 and 6) and Sp1 (middle panel, compare lanes 3 and 7) is seen in HD brain as compared with control brain tissue.

To further examine the strength of huntingtin/Sp1 and huntingtin/TAFII130 interactions in relation to polyglutamine length, we cotransfected HEK 293T cells with expression plasmids for normal (HttQ17) or mutant (HttQ75) full-length huntingtin and flag-tagged Sp1 or hemagglutinin (HA)-tagged TAFII130 (See Methods section). Coimmunoprecipitations of the transfected proteins with antibodies to huntingtin showed that Sp1 preferentially interacted with mutant huntingtin (FIG. 1C), whereas TAFII130 bound similarly to both normal and mutant huntingtin. These results, together with the yeast two-hybrid data, indicate that polyglutamine expansion enhances the interaction of Sp1, but not TAFII130, with huntingtin.

To establish whether huntingtin interacts with Sp1 and TAFII130 in the human brain, coimmunoprecipitation studies were performed using extracts from the caudate nucleus of grade 1 HD brain with antibodies to Sp1 (anti-Sp1) (FIG. 1D), to TAFII130 (anti-TAFII130) (FIG. 1E), or to huntingtin (anti-Htt). Both anti-Sp1 and anti-TAFII130 precipitated huntingtin protein. In addition, anti-Htt coimmunoprecipitated substantial amounts of Sp1 and TAFII130 proteins. We found that the immunoprecipitated complex, in addition to TAFII130, contained other TAFs, suggesting that TAFII130 interacts with huntingtin in the context of TFIID. However, because we found TAFII130 to be expressed at higher levels in HD brain tissue, it is possible that huntingtin interacts with free TAFII130 as well (see below).

Next, we tested whether mutant huntingtin affects the interactions between Sp1 and TAFII130 in HD brain tissue. In coimmunoprecipitation experiments using anti-Sp1 and anti-TAFII130, we found a decrease in the interactions between Sp1 and TAFII130 in the postmortem human HD brain as compared to the control brain (FIG. 1F). These changes in Sp1-TAFII130 interactions were detected in postmortem HD brain tissue from presymptomatic, as well as affected, patients, suggesting early and persistent disruption of Sp1 and TAFII130 functions in the HD brain.

Figure 2C:
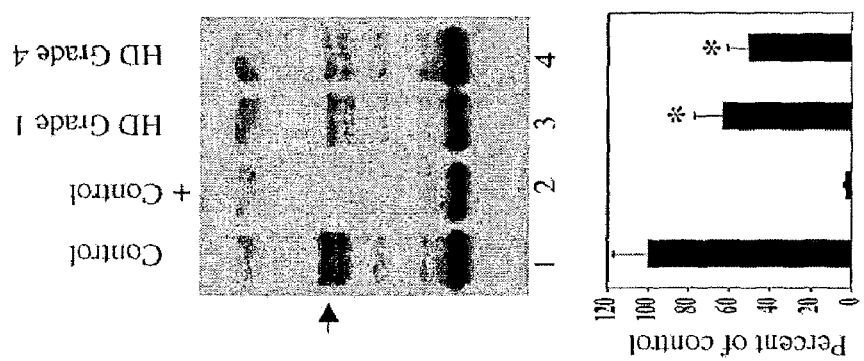
FIG. 2C is a bar graph indicating that binding of Sp1 to the D2 promoter was inhibited in the caudate of the human HD postmortem brain. EMSA was performed with nuclear extracts isolated from presymptomatic grade 1 and grade 4 HD brain tissue as described above herein. Binding of Sp1 to its D2 binding site was decreased by 39% in grade 1 (lane 3) and by 48% in grade 4 HD brain tissue (lane 4) as compared to control brain tissue (lane 1). Competition experiments were performed as in (FIG. 2B) (lane 2).
Figure 2B:
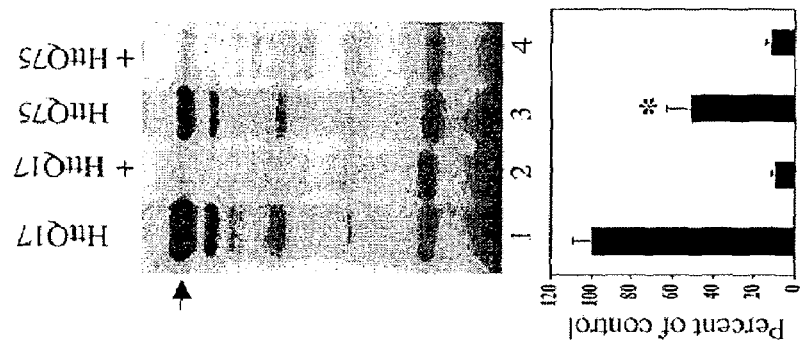
FIG. 2B is a bar graph indicating that mutant huntingtin inhibited binding of Sp1 to the D2 receptor promoter in cultured striatal cells. Primary striatal cells were transfected with wild-type (HttQ 17) or mutant (HttQ75) huntingtin. EMSA was performed with a labeled D2 promoter fragment containing a Sp1 binding site. Mutant huntingtin inhibited binding of Sp1 by 55% (lane 3) as compared to wild-type huntingtin (lane 1). In competition experiments, a 100-fold molar excess of double-stranded nonradioactive oligonucleotide was used (lanes 2 and 4).
Figure 2A:
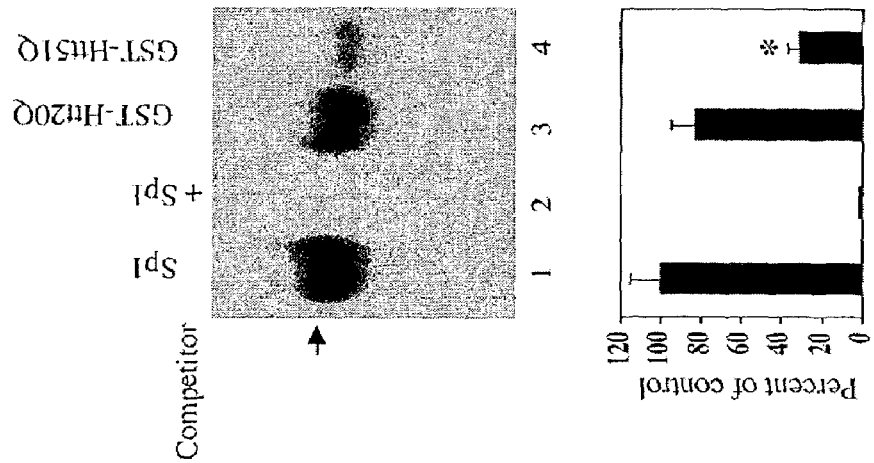
FIG. 2A is a bar graph indicating results of electrophoretic mobility shift assays (EMSAs) with purified Sp1 and glutathione S-transferase (GST)-huntingtin fusion proteins. The level of binding of Sp1 to a labeled consensus Sp1 site is shown in lane 1, and competition with a 50-fold molar excess of unlabelled probe is shown in lane 2 (plus sign). Incubation of Sp1 in the presence of GST-huntingtin with 20 glutamines (Qs) led to a 20% reduction in Sp1 binding (lane 3), whereas huntingtin with 51 Qs inhibited Sp1 binding by 70% (lane 4).

The interaction between huntingtin and Sp1 could also interfere with the DNA binding function of Sp1. To determine the effects of huntingtin on the binding of Sp1 to DNA, we performed an electrophoretic mobility shift assay (EMSA) with purified Sp1 and huntingtin proteins. (See Methods section). Using a consensus Sp1 binding site as a probe, we found a 70% decrease in Sp1 binding to DNA in the presence of mutant huntingtin and a 20% decrease in the presence of wild-type huntingtin (FIG. 2A).

FIG. 2 demonstrates results from experiments that showed mutant huntingtin inhibits the binding of Sp1 to DNA in vitro and in vivo. FIG. 2A shows results of EMSAs with purified Sp1 and glutathione S-transferase (GST)-huntingtin fusion proteins. Binding of Sp1 to a labeled consensus Sp1 site is shown in lane 1, and competition with a 50-fold molar excess of unlabelled probe is shown in lane 2 (plus sign). Incubation of Sp1 in the presence of GST-huntingtin with 20 glutamines (Qs) led to a 20% reduction in Sp1 binding (lane 3), whereas huntingtin with 51 Qs inhibited Sp1 binding by 70% (lane 4). The Sp1/DNA complex was identified with anti-Sp1 and is indicated by an arrow in all panels. FIG. 2B shows that mutant huntingtin inhibited binding of Sp1 to the D2 receptor promoter in cultured striatal cells. Primary striatal cells were transfected with wild-type (HttQ 17) or mutant (HttQ75) huntingtin. EMSA was performed with a labeled D2 promoter fragment containing a Sp1 binding site. Mutant huntingtin inhibited binding of Sp1 by 55% (lane 3) as compared to wild-type huntingtin (lane 1). In competition experiments, a 100-fold molar excess of double-stranded nonradioactive oligonucleotide was used (lanes 2 and 4). FIG. 2C shows results indicating that binding of Sp1 to the D2 promoter was inhibited in the caudate of the human HD postmortem brain. EMSA was performed with nuclear extracts isolated from presymptomatic grade 1 and grade 4 HD brain tissue as described above herein. Binding of Sp1 to its D2 binding site was decreased by 39% in grade 1 (lane 3) and by 48% in grade 4 HD brain tissue (lane 4) as compared to control brain tissue (lane 1). Competition experiments were performed as in (FIG. 2B) (lane 2). FIG. 2D shows results indicating that binding of Sp1 to the D2 promoter fragment in the hippocampus of HD brain (lane 2) was not significantly altered as compared to control (lane 1). EMSA was performed as in FIG. 2C. Competition with unlabeled probe is shown in lane 3. Densitometry was used to quantify the band intensities in all panels (shown as a graph below the respective autoradiogram). Values are expressed as percent of Sp1 binding shown in lane 1 and represent means±SEM of three independent experiments, *P<0.001 for comparison with lane 1 in (A), *P<0.01 in FIGS. 1B and C.

We had previously shown that Sp1 plays a critical role in the regulation of D2 dopamine receptor gene transcription (S. Yajima, et al., *DNA Cell Biol.* 17:471, 1998). Thus, we tested whether alterations in Sp1 function may be responsible for the down-regulation of D2 gene expression in HD. To examine whether mutant huntingtin affects Sp1 binding to the D2 promoter in striatal cells, we performed EMSA using nuclear extracts from primary striatal neurons transfected with wild-type (HttQ17) or mutant (HttQ75) huntingtin as described in the Methods section. Using a region of the D2 dopamine receptor promoter as a probe, we found decreased Sp1 binding in extracts expressing mutant huntingtin as compared with wild-type huntingtin (FIG. 2B). Down-regulation of D2 receptor expression has also been reported in the striata of presymptomatic, as well as affected, HD patients (S. J. Augood, et al., *Ann. Neurol.* 42:215, 1997; R. A. Weeks et al., *Ann. Neurol.* 40:49, 1996). Therefore, we performed EMSA using nuclear extracts isolated from the caudate and hippocampus of grade 1 and grade 4 HD brains. In grades 1 and 2 of HD, there is mild to moderate neuronal loss in the caudate nucleus, whereas the hippocampus remains relatively unaffected until later in the disease. In grade 4, the striatum, as well as other brain regions, is severely atrophic and depleted of 95% or more of its neurons (J. P. Vonsattel et al., *J. Neuropathol. Exp. Neurol.* 44:559, 1985). Using Sp1 binding sites in the D2 promoter as a labeled probe, we found a significant decrease in the DNA binding activity of Sp1 in the caudate nucleus of presymptomatic grade 1 HD brain tissue as compared with control brain tissue (FIG. 2C, lane 3). Similar decreases in Sp1 binding were found in extracts from grade 4 HD brain caudate (FIG. 2C, lane 4), suggesting early and persistent inhibition of Sp1 function. Binding of another transcription factor, MEF2C, to DNA was not changed in these extracts, arguing against nonspecific inhibitory effects of the extracts from HD brain tissue. Our results demonstrated that binding of MEF2 transcription factor to DNA is not altered in caudate of HD brain. In this experiment, nuclear extracts were prepared from the caudate of human control (lane 1) or HD brain (lane 3) and EMSA was performed as in FIG. 2C. Competition with unlabeled probe is shown in lanes 2 and 4. The probe was a double-stranded oligonucleotide containing the brain creatine kinase MEF2 binding site (underlined) (5'-ATGGGC$\underline{TATAAATA}$GCCGCCA-3', SEQ ID NO:5). To determine the specificity of retarded bands we performed supershift experiments with antibodies against MEF2C and MEF2A proteins. When EMSA was performed with nuclear extracts from the hippocampus of grade 1 HD brain tissue, no decrease in Sp1 binding was observed (FIG. 2D). The caudate-specific inhibition of Sp1 function may be, in part, due to the preferential accumulation of mutant huntingtin in the striatum in early stages of HD (L. M. Mende-Mueller, et al., *J. Neurosci.* 21:1830, 2001; H. S. Li, et al., *Nature Genet.* 25:385, 2000).

Figure 3A:
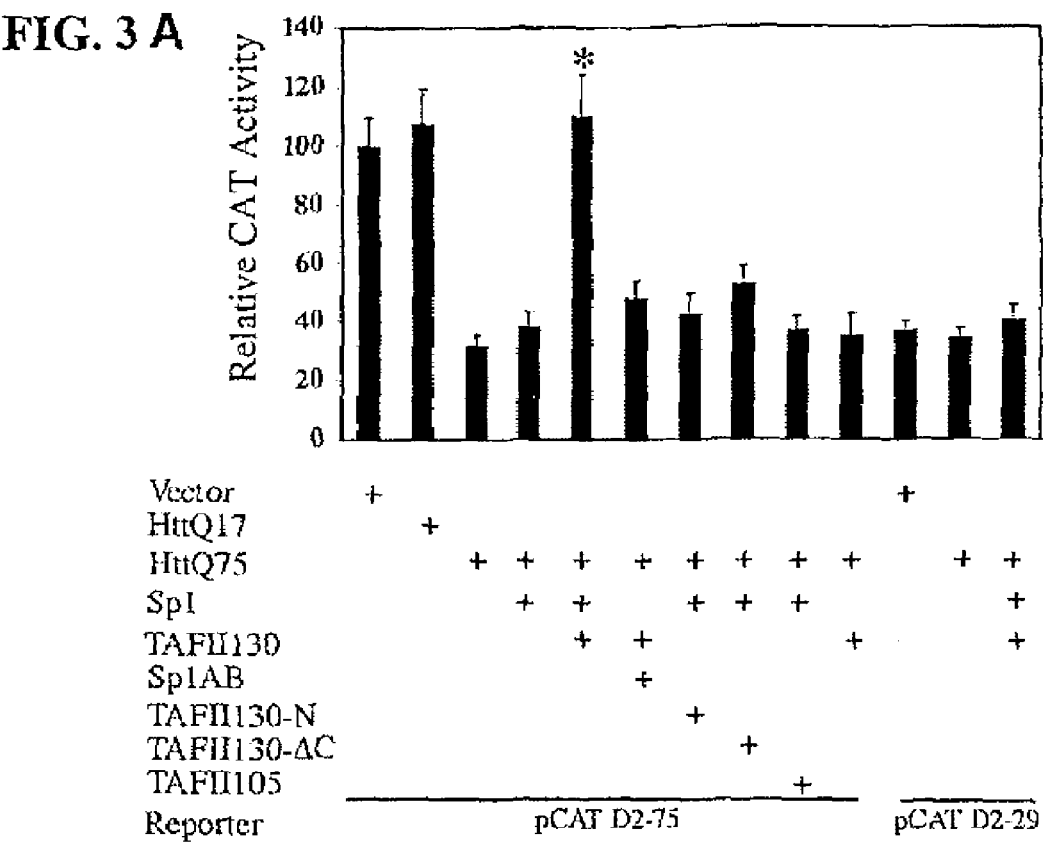
FIG. 3A is a graph indicating effects of Sp1 and TAFII130 on huntingtin-induced repression of the D2 promoter. Primary striatal cultures were transfected with D2 promoter-reporter gene constructs containing a functional Sp1 site (pCAT D2-75) or lacking an Sp1 site (pCAT D2-29). Full-length Sp1 and TAFII130 completely reversed mutant huntingtin (HttQ75)-induced inhibition of D2 promoter activity. TAFII130-N, which contains the $NH_2$-terminal domain of TAFII130 (amino acids 1 through 297), or TAFII130-ΔC (amino acids 1 through 700), which contains both the $NH_2$-terminal domain and the middle domain but lacks the COOH-terminal domain of TAFII130, and Sp1 lacking the DNA binding domain (Sp1AB, amino acids 83 through 621) did not significantly alter D2 promoter activity. Overexpression of TAFII105 or TAFII55 together with Sp1 did not prevent mutant huntingtin-mediated repression. The relative CAT activity in cells transfected with vector alone is arbitrarily shown as 100±SEM. Graphs show means±SEM of at least five independent experiments, *P<0.001 versus HttQ75.
Figure 3B:
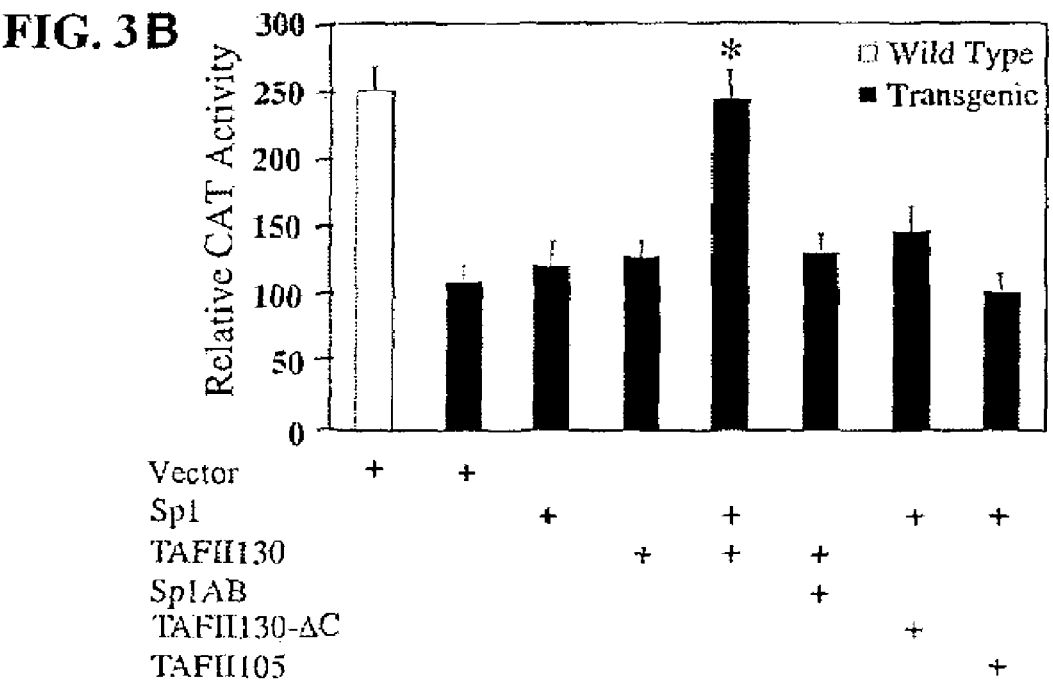
FIG. 3B is a graph indicating that overexpression of both TAFII130 and Sp1 in transgenic striatal cells reverses the effects of mutant huntingtin on D2 promoter activity. Striatal neurons were isolated from HD transgenic mice (solid bars) or from wild-type littermates (open bar). Experiments were performed and analyzed as in FIG. 3A. *P<0.01 versus transgenic control.
Figure 3C:
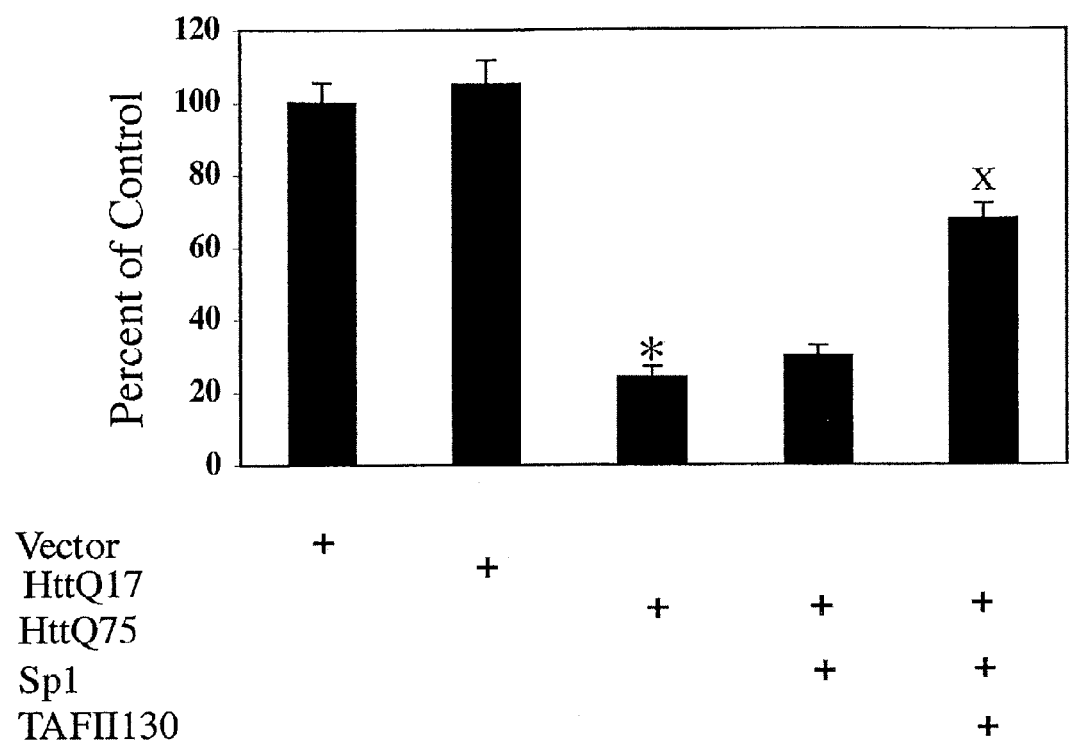
FIG. 3C is a graph of results from analysis of endogenous D2 receptor mRNA in transfected striatal neurons. Primary striatal cultures were transfected as in FIG. 3A, and the levels of D2 mRNA were determined by real-time reverse transcription polymerase chain reaction. The values are presented as percent change as compared to untransfected or vector-transfected striatal cells (set to 100%) (*P<0.001 versus control, ˣP<0.01 versus HttQ75, analysis of variance; data are from three independent experiments). All values were normalized to β-actin, whose mRNA expression was not changed in transfected neurons.

To further establish the role of huntingtin in Sp1-mediated transcription, primary striatal neurons were transfected with D2 promoter-reporter gene constructs along with mutant or normal huntingtin as described above herein. Although huntingtin with normal glutamine repeats (HttQ17) had no significant effect on promoter activity, mutant huntingtin (HttQ75) produced significant inhibition (FIG. 3A). To determine whether the inhibition of Sp1-mediated transcription was dependent on increased levels of huntingtin relative to those of endogenous Sp1 and TAFII130, we overexpressed Sp1 and/or TAFII130 together with huntingtin. We found that overexpression of either Sp1 or TAFII130 alone did not significantly alter the inhibitory effects of mutant huntingtin, whereas coexpression of TAFII130 and Sp1 resulted in complete reversal of huntingtin-induced inhibition of D2 promoter activity (FIG. 3A). These effects of Sp1 and TAFII130 were dependent on Sp1 binding to the D2 promoter, because no significant effect was seen when the Sp1 functional site was deleted (pCAT D2–29) or when an Sp1 expression vector lacking the DNA binding domain (Sp1AB) was used. Similarly, no effect on promoter activity was seen with the NH$_2$-terminus of TAFII130, which does not affect Sp1 activity (D. Saluja, et al., *Mol. Cell Biol.* 18:5734, 1998) and does not interact with huntingtin (FIG. 1B). These results suggest that mutant huntingtin inhibits Sp1-mediated transcription by interfering with Sp1/TAFII130 function. To confirm that these effects on the D2 promoter are specific, we examined whether TAFII105, a human TAF closely related to TAFII130 (R. Dikstein, et al., *Cell* 87:137, 1996), and TAFII55, which binds Sp1 (C. M. Chiang and R. G. Roeder, *Science* 267:531, 1995), affect huntingtin-mediated inhibition of the D2 promoter. When TAFII105 or TAFII55 was overexpressed together with Sp1 and mutant huntingtin in striatal cells, no significant effect was observed on D2 promoter activity (FIG. 3A). To determine whether these effects of mutant huntingtin on the D2 promoter may simply be due to nonphysiological concentrations of overexpressed huntingtin, we performed similar experiments in striatal neurons isolated from transgenic HD mice as described above herein. These mice express relatively low steady-state levels of mutant huntingtin (NH$_2$-terminal fragment) with 82 glutamine repeats (J. K. Copper, et al., *Hum. Mol. Genet.* 7:783, 1998). When these cultured striatal cells were transfected with D2 promoter constructs, similar inhibition of promoter activity was observed as in experiments where mutant huntingtin was overexpressed by transient transfection. Furthermore, overexpression of Sp1 and TAFII130 resulted in complete reversal of D2 promoter inhibition in cells derived from transgenic HD mice (FIG. 3B). As before, these effects of Sp1 and TAFII130 were dependent on Sp1 binding to its functional site on the D2 promoter. Because no toxicity was observed in cells isolated from the transgenic animals, it is unlikely that the observed decrease in transcription is a consequence of cellular toxicity caused by mutant huntingtin. To determine whether the transfection of mutant huntingtin affects endogenous D2 receptors in primary striatal neurons, we analyzed D2 mRNA levels in transfected cells (See Methods section). The presence of mutant huntingtin resulted in decreased expression of D2 mRNA as compared to the wild-type huntingtin. This inhibitory effect of mutant huntingtin on the endogenous D2 receptor was partially reversed by overexpression of TAFII130 and Sp1 in striatal cells (FIG. 3C). To determine whether these changes in D2 receptor mRNA lead to altered protein levels, we analyzed the expression of D2 receptors in transfected striatal neurons by immunocytochemistry, using antibody to D2 (See Methods section). We found that transfection of mutant huntingtin resulted in a robust decrease of D2 expression in about 70% of transfected striatal neurons, whereas neurons cotransfected with Sp1, TAFII130, and mutant huntingtin showed normal D2 expression. Taken together, these results suggest that mutant huntingtin specifically represses D2 receptor gene expression in a Sp1/TAFII130-dependent manner.

FIG. 3 illustrates that mutant huntingtin-mediated repression of the D2 receptor promoter and cell death are prevented by overexpression of Sp1 and TAFII130 in striatal cultures. FIG. 3A shows effects of Sp1 and TAFII130 on huntingtin-induced repression of the D2 promoter. Primary striatal cultures were transfected as described above herein with D2 promoter-reporter gene constructs containing a functional Sp1 site (pCAT D2-75) or lacking an Sp1 site (pCAT D2-29). Full-length Sp1 and TAFII130 completely reversed mutant huntingtin (HttQ75)-induced inhibition of D2 promoter activity. TAFII130-N, which contains the $NH_2$-terminal domain of TAFII130 (amino acids 1 through 297), or TAFII130-ΔC (amino acids 1 through 700), which contains both the N-$H_2$-terminal domain and the middle domain but lacks the COOH-terminal domain of TAFII130, and Sp1 lacking the DNA binding domain (Sp1AB, amino acids 83 through 621) did not significantly alter D2 promoter activity. Overexpression of TAFII105 or TAFII55 together with Sp1 did not prevent mutant huntingtin-mediated repression. The relative CAT activity in cells transfected with vector alone is arbitrarily shown as 100±SEM. Graphs show means±SEM of at least five independent experiments, *$P<0.001$ versus HttQ75. FIG. 3B shows overexpression of both TAFII130 and Sp1 in transgenic striatal cells reverses the effects of mutant huntingtin on D2 promoter activity. Striatal neurons were isolated from HD transgenic mice (solid bars) or from wild-type littermates (open bar). Experiments were performed and analyzed as in FIG. 3A. *$P<0.01$ versus transgenic control. FIG. 3C shows analysis of endogenous D2 receptor mRNA in transfected striatal neurons. Primary striatal cultures were transfected as in FIG. 3A, and the levels of D2 mRNA were determined by real-time reverse transcription polymerase chain reaction. The values are presented as percent change as compared to untransfected or vector-transfected striatal cells (set to 100%) (*$P<0.001$ versus control, *$P<0.01$ versus HttQ75, analysis of variance; data are from three independent experiments). All values were normalized to β-actin, whose mRNA expression was not changed in transfected neurons. Our experimental results also illustrated that mutant huntingtin-induced decrease of D2 dopamine receptor expression is prevented by overexpression of Sp1 and TAFII130 in striatal neurons. A series of experiments were performed in which neurons were stained for the mutant huntingtin (FLAG epitope), for the D2receptor, and for TAFII130 (HA epitope). Decreased D2 staining is shown in neurons transfected with huntingtin alone. No change in D2 staining was observed in neurons transfected with huntingtin, TAFII130, and Sp1. FIG. 3D shows that Sp1 and TAFII130 together protect against mutant huntingtin-induced striatal toxicity. Primary striatal cultures were isolated and transfected with the expression plasmids as in FIG. 3A. Mutant huntingtin-induced cell death was significantly prevented by overexpression of both Sp1 and TAFII130. All values are expressed as means±SEM, *$P<0.01$ compared to HttQ75.

Figure 3D:
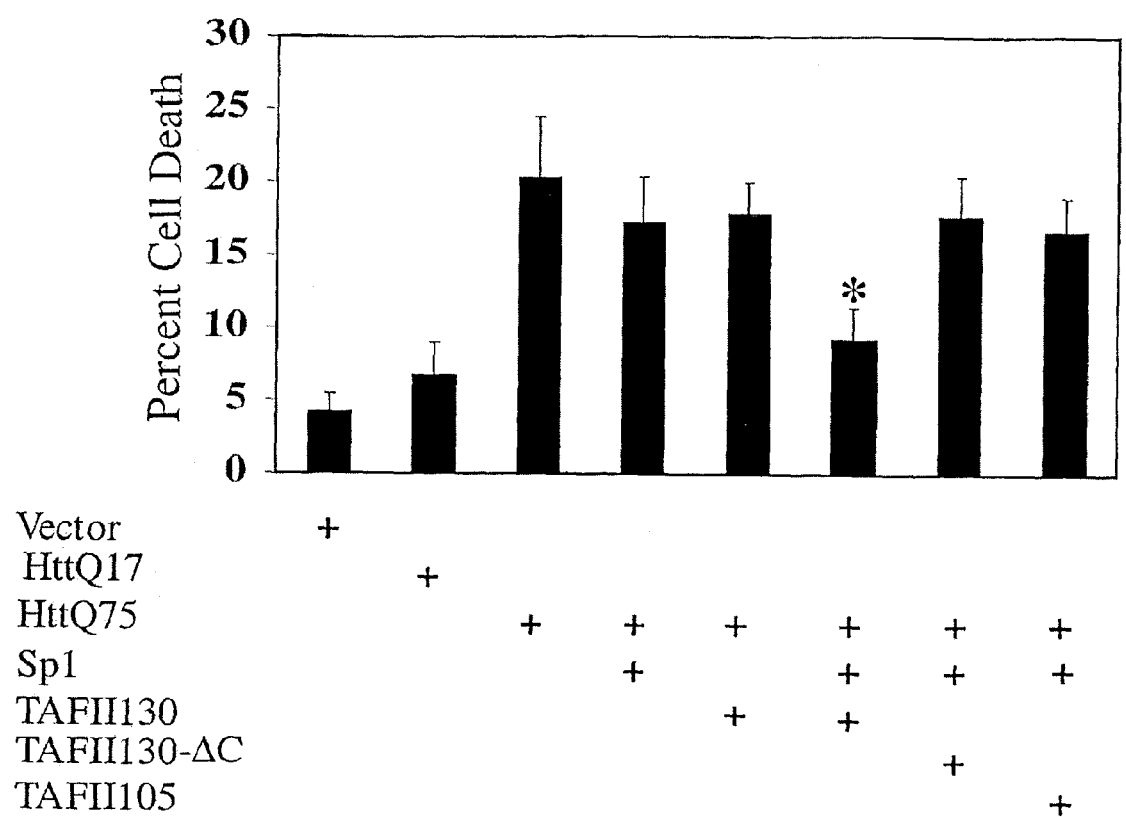
FIG. 3D is a graph indicating that Sp1 and TAFII130 together protect against mutant huntingtin-induced striatal toxicity. Primary striatal cultures were isolated and transfected with the expression plasmids as in FIG. 3A. Mutant huntingtin-induced cell death was significantly prevented by overexpression of both Sp1 and TAFII130. All values are expressed as means±SEM, *P<0.01 compared to HttQ75.

Next, we investigated the potential role of mutant huntingtin's interactions with Sp1 and TAFII130 in relation to cellulartoxicity. Previous experiments demonstrated that mutant huntingtin is toxic when overexpressed in cultured striatal cells (F. Saudou, et al., Cell 95:55, 1998). Here, we show that when full-length mutant huntingtin (HttQ75) was expressed in striatal neurons together with Sp1 and TAFII130, huntingtin-mediated toxicity was almost completely abrogated, whereas transfection of either Sp1 or TAFII130 alone resulted in minimal, statistically insignificant protection (FIG. 3D). To further establish the role of TAFII130 in huntingtin-induced cell death, we tested whether neurons could be protected against mutant huntingtin by transfecting TAFII130 lacking the COOH-terminal domain (TAFII130-ΔC). The COOH terminus of TAFII130 has been shown to mediate interactions with transcriptional activators, with other TAFs in TFIID (Y. G. Gangloff, et al., Mol. Cell. Biol. 20:340, 2000;, T. Furukawa and N. Tanese, J. Biol. Chem. 275:29847, 2000), and with huntingtin (FIG. 1B). We found that coexpression of TAFII130-ΔC with Sp1 failed to block huntingtin-induced cell death (FIG. 3M). To determine whether the effects of TAFII130 on neuronal survival are specific, we tested TAFII105, which is structurally similar to TAFII130 (R. Dikstein, et al., Cell 87:137, 1996). When transfected along with Sp1 and mutant huntingtin, TAFII105 did not significantly protect neurons from huntingtin-mediated toxicity.

It has previously been suggested that huntingtin interferes with gene transcription by depleting transcription factors from their normal location and sequestering them into nuclear aggregates (A. Kazantsev, et al., Proc. Natl. Acad. Sci. U.S.A. 96:11404, 1999, J. S. Steffan, et al., Proc. Natl. Acad. Sci. U.S.A. 97: 6763 (2000), F. C. Nucifora, et al., Science 291:2423, 2001, C. C. Huang, et al., Somatic Cell Mol. Genet. 24:971, 1998). To examine whether the function of Sp1 is compromised through sequestration into nuclear inclusions, we performed immunocytochemistry on transgenic HD mice and human postmortem HD brains. Nuclear and cytoplasmic inclusions were strongly labeled with an antibody to the $NH_2$-terminus of huntingtin that specifically labels huntingtin aggregates, whereas Sp1 staining was not detected in these inclusions, suggesting that the soluble rather than the aggregated form of huntingtin interacts with Sp1 (FIGS. 4A–D). This finding was confirmed by Western blot analysis, showing a robust increase of Sp1 protein in the soluble fraction of caudate tissue from postmortem HD brains (FIG. 4E). Sp1 protein levels were also increased in the cerebral cortex but decreased in the hippocampus (FIG. 4F). To determine whether these changes were specific for Sp1, we examined TAFII130 protein levels as well as TAFII250 and the unrelated transcription factor MEF2C. Although TAFII130 showed an expression pattern similar to that of Sp1 (FIG. 4F), no increases in TAFII250 or MEF2C were detected in the caudate of HD brains (FIG. 4G). To exclude the possibility that these increases in Sp1 and TAFII130 represent a stress response in the diseased striatum, we examined Sp1 and TAFII130 levels in another neurodegenerative disease, progressive supranuclear palsy (PSP), which also affects the caudate nucleus. No changes in the expression of Sp1 or TAFII130 were detected in the caudate nucleus of PSP brain tissue. We determined that levels of Sp1 and TAFII130 proteins are not altered in the caudate nucleus of PSP postmortem brain. For this experiment, Triton X-insoluble protein fractions were collected from caudate nucleus of human control brain and PSP brain and Western blot analysis was performed as in FIG. 4E. Densitometric analysis was performed to correct for differences in the expression of tubulin. Expression of TAFII130 and Sp1 was not significantly different in control and PSP brain. Our finding that Sp1 and TAFII130 were specifically increased in the caudate nucleus but not the hippocampus in HD brains may represent a compensatory response to the inhibition of Sp1-regulated transcriptional activity in the presence of mutant huntingtin.

FIG. 4 illustrates the presence of increased levels of Sp1 and TAFII130 in the caudate of the human HD brain. FIGS. 4A–D show that Sp1 is not present in huntingtin-positive nuclear or cytoplasmic inclusions in human or transgenic HD brains. Immunohistochemistry using EM48, an antibody specific for huntingtin aggregates, shows labeling of inclusions (arrows) in postmortem grade 1 human HD brain tissue (frontal cortex, panel a) and transgenic mouse HD brain tissue (pyriform cortex, panel c) (K. B. Kegel, et al., *J. Biol. Chem.* 277:7466, 2002). Adjacent sections show diffuse nuclear and cytoplasmic localization of Sp1 but no evident localization of Sp1 in huntingtin aggregates. FIG. 4E shows levels of Sp1 protein are increased in the caudate nucleus of grade 1 and grade 4 HD brains. Soluble protein fractions were collected from the caudate nucleus of a human control brain (lane 1), from a grade 1 HD brain (lane 2), and from a grade 4 HD brain (lane 3), and Western blot analysis was performed. Densitometric analysis shows that in grade 1 HD brain tissue as compared to control brain tissue, Sp1 levels are increased by 6.1 fold (compare lanes 1 and 2) and in grade 4 HD brain tissue by 2.8 fold (compare lanes 1 and 3). The brain samples used in each group were derived from postmortem tissue described in FIG. 2C. Densitometric analysis was corrected for differences in the expression of tubulin. Values are shown as fold above control. FIG. 4C shows expression levels of Sp1 and TAFII130 in different regions of an HD brain. Postmortem brain tissues were processed and analyzed as in FIG. 4E. As compared with the control brain (caudate) (lane 1), the HD brain has increased Sp1 protein in the caudate nucleus (lane 3) and cerebral cortex (lane 2) but decreased Sp1 protein in the hippocampus (lane 4). TAFII130 expression follows a similar pattern as Sp1, except that only the caudate nucleus shows a marked increase in TAFII130 expression levels (compare lanes 1 and 3). FIG. 4G shows expression of MEF2C and TAFII250 in human HD brain tissue. Tissues were processed and analyzed as in FIG. 4E. Expression of TAFII250 was not different in control (lane 1) and HD brains (lane 2), whereas MEF2C levels showed about a 30% decrease in HD brain tissue.

Together, the DNA binding and protein expression data suggest that the decreased function of Sp1 in HD is not due to sequestration of Sp1 into aggregates but rather to the inhibition of Sp1 by soluble mutant huntingtin. Our data are consistent with the finding of Li et al., who recently showed that the soluble form of mutant huntingtin binds more tightly to Sp1 than does aggregated huntingtin (S.-H. Li, et al., *Mol. Cell. Biol.* 22:1277, 2002).

Figure 5:
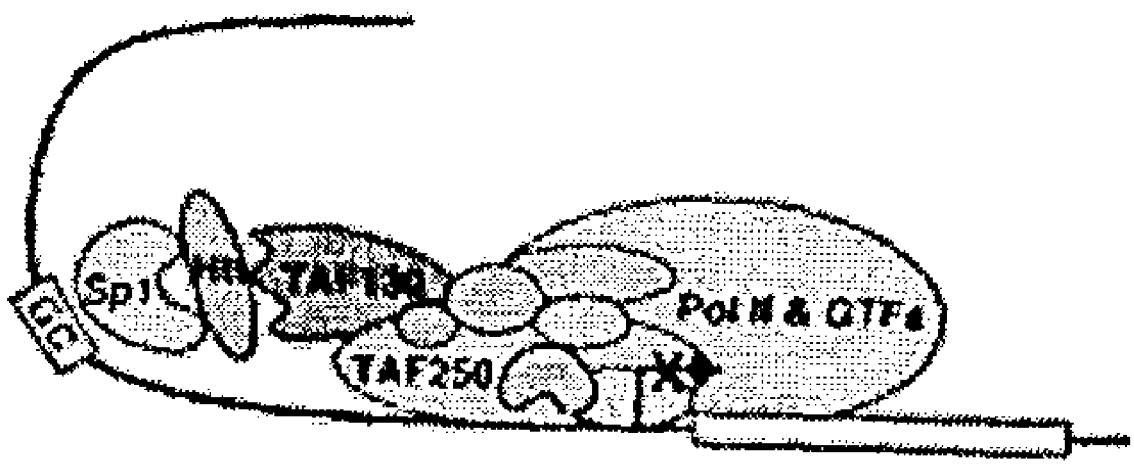
FIG. 5 is a diagram of a model depicting transcriptional downregulation of Sp1-dependent genes in HD brain.

We found that huntingtin interacts with both the glutamine-rich and the COOH-terminal domain of TAFII130 and that the COOH-terminal domain is involved in protection against huntingtin-induced transcriptional dysregulation and neuronal cell death. The conserved COOH-terminal domain of TAFII130 participates in a number of protein-protein interactions, including several TAFs in the TFIID complex (Y. G. Gangloff, et al., *Mol. Cell. Biol.* 20:340, 2000; T. Furukawa and N. Tanese, *J. Biol. Chem.* 275:29847, 2000). These findings and the recent report that atrophin, which causes another polyglutamine disease (DRPLA), also binds to the COOH-terminal domain of TAFII130 (G. Shimohata, et al., *Nat. Genet.* 26:29, 2000), suggest that by competing with the critical protein interaction surface of TAFII130, polyglutamine stretches may interfere with the coupling of activator-mediated signals to the basal transcriptional machinery (FIG. 5). FIG. 5 is a diagram of a model depicting transcriptional downregulation of Sp1-dependent genes in HD brain. We propose that soluble mutant huntingtin (Htt) contributes to loss of Sp1 binding to DNA and disruption of Sp1/TAFII130 activation function leading to transcriptional dysregulation in early stages of Huntington's Disease. The contributions of TAFII130 as well as of other TAFs to gene transcription are likely to be promoter- and cell type-specific. Consistent with this idea is the finding that expression of TAFII130 varies in different regions of the central nervous system and during development (M. Metsis, et al., *Exp. Cell Res.* 269:214, 2001), and the fact that certain TAFs appear to be required for the transcription of a subset of genes (S. R. Albright and R. Tjian, *Gene* 242:1, 2000).

Gene expression analyses on DNA microarrays have shown that differential alterations in gene expression occur in transgenic HD mice as compared with wild-type mice at an early symptomatic stage (R. Luthi-Carter, et al., *Hum. Mol. Genet.* 29:1259, 2000). We have determined that a prominent feature of these changes in gene expression is the down-regulation of genes containing putative Sp1 binding sites in their promoters, suggesting that loss of Sp1 binding and disruption of Sp1/TAFII130 activation function in early HD may lead to changes in the expression of a number of downstream genes.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

The invention claimed is:

1. A method for identifying compounds in vitro that modulate dysregulation of transcription mediated by a mutant huntingtin protein with an expanded polyglutamine tract through Sp1 and TAFII130 comprising the steps of:

provoding a transcriptional assay system, comprising Sp1, TAFII130, the mutant huntingtin protein and a double-stranded DNA sequence comprising the Sp1 promoter operably linked to a detectable sequence all within a neuronal cell, contacting the assay system with a candidate pharmacological agent, and measuring the amount of mRNA transcript of the detectable sequence, wherein a change in the amount of the transcript compared to a control is indicative of the modulation by the candidate pharmacological agent of the dysregulation of transcription mediated by mutant huntingtin protein through Sp1 and TAFII130.

2. The method of claim 1, wherein the candidate pharmacological agent increases the amount of mRNA transcript of the detectable sequence compared to the control.

3. The method of claim 1, wherein the candidate pharmacological agent decreases the amount of mRNA transcript of the detectable sequence compared to the control.

* * * * *

UNITED STATES PATENT AND TRADEMARK OFFICE
CERTIFICATE OF CORRECTION

PATENT NO. : 7,045,306 B2
APPLICATION NO. : 10/425175
DATED : May 16, 2006
INVENTOR(S) : Dimitri Krainc It is certified that error appears in the above-identified patent and that said Letters Patent is hereby corrected as shown below:

On the title page, item [54] should read:

METHOD FOR IDENTIFYING COMPOUNDS IN VITRO THAT MODULATE THE DYSREGULATION OF TRANSCRIPTION MEDIATED BY MUTANT HUNTINGTIN PROTEIN

Signed and Sealed this

First Day of August, 2006

JON W. DUDAS
*Director of the United States Patent and Trademark Office*